US010136997B2

(12) United States Patent
Yager

(10) Patent No.: US 10,136,997 B2
(45) Date of Patent: Nov. 27, 2018

(54) TIBIAL PROSTHESIS FOR TIBIA WITH VARUS RESECTION

(71) Applicant: Zimmer, Inc., Warsaw, IN (US)

(72) Inventor: Edward R. Yager, Fort Wayne, IN (US)

(73) Assignee: Zimmer, Inc., Warsaw, IN (US)

(*) Notice: Subject to any disclaimer, the term of this patent is extended or adjusted under 35 U.S.C. 154(b) by 0 days.

(21) Appl. No.: 15/267,826

(22) Filed: Sep. 16, 2016

(65) Prior Publication Data

US 2017/0086982 A1 Mar. 30, 2017

Related U.S. Application Data

(60) Provisional application No. 62/234,141, filed on Sep. 29, 2015.

(51) Int. Cl.
*A61F 2/38* (2006.01)
*A61F 2/30* (2006.01)

(52) U.S. Cl.
CPC .......... *A61F 2/389* (2013.01); *A61F 2/30749* (2013.01); *A61F 2002/30133* (2013.01)

(58) Field of Classification Search
CPC ............................... A61F 2/389; A61F 2/3868
See application file for complete search history.

(56) References Cited

U.S. PATENT DOCUMENTS

| 4,081,866 A | 4/1978 | Upshaw et al. |
| 4,340,978 A | 7/1982 | Buechel et al. |
| 4,662,889 A | 5/1987 | Zichner et al. |
| 4,888,020 A | 12/1989 | Horber |
| 4,944,756 A | 7/1990 | Kenna |
| 4,950,298 A | 8/1990 | Gustilo et al. |
| 4,959,071 A | 9/1990 | Brown et al. |
| 5,007,933 A | 4/1991 | Sidebotham et al. |

(Continued)

FOREIGN PATENT DOCUMENTS

| AU | 2006325787 B2 | 10/2013 |
| CA | 2641966 C | 11/2016 |

(Continued)

OTHER PUBLICATIONS

"U.S. Appl. No. 11/611,021, Notice of Allowance dated Nov. 4, 2016", 10 pgs.

(Continued)

*Primary Examiner* — Jason-Dennis Stewart
(74) *Attorney, Agent, or Firm* — Schwegman Lundberg & Woessner, P.A.

(57) ABSTRACT

Methods, systems and apparatuses are disclosed including apparatuses that can be used in a total knee replacement procedure. According to one example, a tibial implant is disclosed. The tibial implant can be configured for attachment to a tibia in a knee arthroplasty and can include a baseplate having a lateral portion and a medial portion oriented relative to an anteroposterior axis and a fixation member. Each of the lateral portion and the medial portion can have a distal surface configured to interface with a resected proximal surface of a tibia. The fixation member can be coupled to and extend both distally and medially from the baseplate such that the fixation member is oriented at an acute angle relative to the distal surface of the medial portion.

17 Claims, 8 Drawing Sheets

(56) References Cited

U.S. PATENT DOCUMENTS

| | | |
|---|---|---|
| 5,061,271 A | 10/1991 | Van Zile |
| 5,133,758 A | 7/1992 | Hollister |
| 5,133,760 A * | 7/1992 | Petersen .............. A61F 2/3676 623/20.34 |
| 5,137,536 A | 8/1992 | Koshino |
| 5,226,915 A | 7/1993 | Bertin |
| 5,282,861 A | 2/1994 | Kaplan |
| 5,282,869 A | 2/1994 | Miyajima et al. |
| 5,326,361 A | 7/1994 | Hollister |
| 5,330,532 A | 7/1994 | Ranawat |
| 5,445,642 A | 8/1995 | McNulty et al. |
| 5,549,686 A | 8/1996 | Johnson et al. |
| 5,549,688 A | 8/1996 | Ries et al. |
| 5,609,643 A | 3/1997 | Colleran et al. |
| 5,681,354 A | 10/1997 | Eckhoff |
| 5,688,279 A | 11/1997 | McNulty et al. |
| 5,702,460 A | 12/1997 | Carls et al. |
| 5,728,162 A | 3/1998 | Eckhoff |
| 5,776,201 A | 7/1998 | Colleran et al. |
| 5,824,105 A | 10/1998 | Ries et al. |
| 5,871,546 A | 2/1999 | Colleran et al. |
| 5,879,354 A | 3/1999 | Haines et al. |
| 5,879,393 A | 3/1999 | Whiteside et al. |
| 5,935,173 A | 8/1999 | Roger et al. |
| 6,013,103 A | 1/2000 | Kaufman et al. |
| 6,039,764 A | 3/2000 | Pottenger et al. |
| 6,074,424 A | 6/2000 | Perrone, Jr. et al. |
| 6,096,082 A | 8/2000 | Stegmuller et al. |
| 6,106,529 A | 8/2000 | Techiera |
| 6,152,960 A | 11/2000 | Pappas |
| 6,197,064 B1 | 3/2001 | Haines et al. |
| 6,217,619 B1 | 4/2001 | Keller |
| 6,235,060 B1 | 5/2001 | Kubein-Meesenburg et al. |
| 6,264,697 B1 | 7/2001 | Walker |
| 6,325,828 B1 | 12/2001 | Dennis et al. |
| 6,364,911 B1 | 4/2002 | Schmotzer et al. |
| 6,540,786 B2 | 4/2003 | Chibrac et al. |
| 6,540,787 B2 | 4/2003 | Biegun et al. |
| 6,589,283 B1 | 7/2003 | Metzger et al. |
| 6,616,696 B1 | 9/2003 | Merchant |
| 6,699,291 B1 | 3/2004 | Augoyard et al. |
| 6,712,856 B1 | 3/2004 | Carignan et al. |
| 6,770,099 B2 | 8/2004 | Andriacchi et al. |
| 6,802,865 B2 | 10/2004 | Biegun et al. |
| 6,846,329 B2 | 1/2005 | Mcminn |
| 6,893,467 B1 | 5/2005 | Bercovy |
| 7,081,137 B1 | 7/2006 | Servidio |
| 7,297,164 B2 | 11/2007 | Johnson et al. |
| 7,306,609 B2 | 12/2007 | Schmotzer et al. |
| 7,364,590 B2 | 4/2008 | Siebel |
| 7,413,577 B1 | 8/2008 | Servidio |
| 7,442,196 B2 | 10/2008 | Fisher et al. |
| 7,465,320 B1 | 12/2008 | Kito et al. |
| 7,678,152 B2 | 3/2010 | Suguro et al. |
| 7,691,150 B2 | 4/2010 | Cronin et al. |
| 7,695,520 B2 | 4/2010 | Metzger et al. |
| 7,806,897 B1 | 10/2010 | Bonutti |
| 8,062,377 B2 | 11/2011 | Haines |
| 8,075,626 B2 | 12/2011 | Dun |
| 8,088,167 B2 | 1/2012 | Haines |
| 8,211,181 B2 | 7/2012 | Walker |
| 8,292,964 B2 | 10/2012 | Walker |
| 8,298,288 B2 | 10/2012 | Walker |
| 8,357,202 B2 | 1/2013 | Heggendorn et al. |
| 8,377,141 B2 | 2/2013 | Mcminn |
| 8,394,147 B2 | 3/2013 | Otto et al. |
| 8,409,293 B1 | 4/2013 | Howard et al. |
| 8,480,753 B2 | 7/2013 | Collazo et al. |
| 8,480,754 B2 | 7/2013 | Bojarski et al. |
| 8,500,816 B2 | 8/2013 | Dees, Jr. et al. |
| 8,551,179 B2 | 10/2013 | Jones et al. |
| 8,603,101 B2 | 12/2013 | Claypool et al. |
| 8,721,732 B2 | 5/2014 | Samuelson et al. |
| 8,911,502 B2 | 12/2014 | Li et al. |
| 8,932,365 B2 | 1/2015 | Parisi et al. |
| 9,060,868 B2 | 6/2015 | Parisi et al. |
| 9,173,744 B2 | 11/2015 | Donno et al. |
| 9,308,095 B2 | 4/2016 | Parisi et al. |
| 9,592,127 B2 | 3/2017 | Earl et al. |
| 9,839,521 B2 | 12/2017 | Todd et al. |
| 9,867,708 B2 | 1/2018 | Donno et al. |
| 9,956,048 B2 | 5/2018 | Bojarski et al. |
| 10,045,850 B2 | 8/2018 | Parisi et al. |
| 2003/0153924 A1 | 8/2003 | Kana et al. |
| 2003/0158606 A1 | 8/2003 | Coon et al. |
| 2003/0225458 A1 | 12/2003 | Donkers et al. |
| 2004/0039450 A1 | 2/2004 | Griner et al. |
| 2004/0172137 A1 | 9/2004 | Blaylock et al. |
| 2004/0204766 A1 * | 10/2004 | Siebel ...................... A61F 2/38 623/20.31 |
| 2004/0243245 A1 | 12/2004 | Plumet et al. |
| 2004/0249467 A1 | 12/2004 | Meyers et al. |
| 2005/0055102 A1 | 3/2005 | Tornier et al. |
| 2005/0102032 A1 | 5/2005 | Beynnon et al. |
| 2005/0107884 A1 | 5/2005 | Johnson et al. |
| 2005/0177169 A1 | 8/2005 | Fisher et al. |
| 2005/0283249 A1 | 12/2005 | Carson |
| 2005/0283250 A1 | 12/2005 | Coon et al. |
| 2005/0283251 A1 | 12/2005 | Coon et al. |
| 2005/0283252 A1 | 12/2005 | Coon et al. |
| 2005/0283253 A1 | 12/2005 | Coon et al. |
| 2006/0028773 A1 | 2/2006 | Shimazawa et al. |
| 2006/0129246 A1 | 6/2006 | Steffensmeier |
| 2006/0142774 A1 | 6/2006 | Metzger |
| 2006/0200163 A1 | 9/2006 | Roger et al. |
| 2006/0224244 A1 | 10/2006 | Thomas et al. |
| 2006/0235541 A1 | 10/2006 | Hodorek |
| 2006/0235542 A1 | 10/2006 | Hodorek et al. |
| 2006/0241634 A1 | 10/2006 | Tuttle et al. |
| 2006/0265078 A1 | 11/2006 | Mcminn |
| 2006/0265080 A1 | 11/2006 | Mcminn |
| 2006/0287733 A1 | 12/2006 | Bonutti |
| 2007/0088444 A1 | 4/2007 | Hodorek et al. |
| 2007/0123984 A1 | 5/2007 | Hodorek |
| 2007/0135925 A1 | 6/2007 | Walker |
| 2007/0135926 A1 | 6/2007 | Walker |
| 2007/0150066 A1 | 6/2007 | McMinn et al. |
| 2007/0179607 A1 | 8/2007 | Hodorek et al. |
| 2007/0233269 A1 | 10/2007 | Steines et al. |
| 2007/0260323 A1 | 11/2007 | Earl et al. |
| 2008/0058947 A1 | 3/2008 | Earl et al. |
| 2008/0058948 A1 | 3/2008 | Biegun et al. |
| 2008/0097615 A1 | 4/2008 | Lipman et al. |
| 2008/0097616 A1 | 4/2008 | Meyers et al. |
| 2008/0114463 A1 | 5/2008 | Auger et al. |
| 2008/0119940 A1 | 5/2008 | Otto et al. |
| 2008/0140212 A1 | 6/2008 | Metzger et al. |
| 2008/0188855 A1 | 8/2008 | Brown et al. |
| 2008/0188937 A1 | 8/2008 | Ribic |
| 2008/0188942 A1 | 8/2008 | Brown et al. |
| 2008/0243258 A1 | 10/2008 | Sancheti |
| 2008/0281428 A1 | 11/2008 | Meyers et al. |
| 2008/0288080 A1 | 11/2008 | Sancheti |
| 2009/0036992 A1 | 2/2009 | Tsakonas |
| 2009/0043395 A1 | 2/2009 | Hotokebuchi et al. |
| 2009/0062924 A1 | 3/2009 | Kito et al. |
| 2009/0105772 A1 | 4/2009 | Seebeck et al. |
| 2009/0132055 A1 | 5/2009 | Ferro |
| 2009/0149963 A1 * | 6/2009 | Sekel .................. A61F 2/30721 623/20.15 |
| 2009/0222103 A1 | 9/2009 | Fitz et al. |
| 2009/0265011 A1 | 10/2009 | Mandell |
| 2009/0265013 A1 | 10/2009 | Mandell |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2010/0036499 A1 | 2/2010 | Pinskerova |
| 2010/0036500 A1 | 2/2010 | Heldreth et al. |

(56) References Cited

U.S. PATENT DOCUMENTS

| | | |
|---|---|---|
| 2010/0042224 A1 | 2/2010 | Otto et al. |
| 2010/0161067 A1 | 6/2010 | Saleh et al. |
| 2010/0191298 A1 | 7/2010 | Earl et al. |
| 2010/0211179 A1 | 8/2010 | Angibaud et al. |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0093083 A1 | 4/2011 | Earl et al. |
| 2011/0144760 A1 | 6/2011 | Wong et al. |
| 2011/0218541 A1 | 9/2011 | Bailey et al. |
| 2011/0307067 A1 | 12/2011 | Dees |
| 2012/0089234 A1 | 4/2012 | Mouillet et al. |
| 2012/0203350 A1 | 8/2012 | Hagen et al. |
| 2012/0310362 A1 | 12/2012 | Li et al. |
| 2012/0323334 A1 | 12/2012 | Jones et al. |
| 2012/0323335 A1 | 12/2012 | Parisi et al. |
| 2012/0323336 A1 | 12/2012 | Parisi et al. |
| 2012/0323337 A1 | 12/2012 | Parisi et al. |
| 2013/0006370 A1 | 1/2013 | Wogoman et al. |
| 2013/0006371 A1 | 1/2013 | Wogoman et al. |
| 2013/0006376 A1 | 1/2013 | Wogoman et al. |
| 2013/0006378 A1 | 1/2013 | Wogoman |
| 2013/0024001 A1 | 1/2013 | Wentorf et al. |
| 2013/0035765 A1 | 2/2013 | Dacus |
| 2013/0197653 A1 | 8/2013 | Hawkins et al. |
| 2013/0204380 A1 | 8/2013 | Mouillet et al. |
| 2013/0211532 A1 | 8/2013 | Samuelson et al. |
| 2013/0218284 A1 | 8/2013 | Eickmann et al. |
| 2013/0226305 A1 | 8/2013 | Donno et al. |
| 2013/0345821 A1 | 12/2013 | Jones et al. |
| 2014/0025081 A1 | 1/2014 | Lorio et al. |
| 2014/0128973 A1 | 5/2014 | Howard et al. |
| 2014/0142713 A1 | 5/2014 | Wright et al. |
| 2014/0228851 A1 | 8/2014 | Guloy, Jr. et al. |
| 2015/0045801 A1 | 2/2015 | Axelson, Jr. et al. |
| 2015/0081031 A1 | 3/2015 | Parisi et al. |
| 2015/0265410 A1 | 9/2015 | Parisi et al. |
| 2015/0374500 A1 | 12/2015 | Donno et al. |
| 2016/0030053 A1 | 2/2016 | Yager et al. |
| 2016/0220379 A1 | 8/2016 | Parisi et al. |
| 2016/0270856 A1 | 9/2016 | Park et al. |
| 2016/0278873 A1 | 9/2016 | Fisher et al. |
| 2017/0156872 A1 | 6/2017 | Earl et al. |
| 2018/0064543 A1 | 3/2018 | Wright et al. |
| 2018/0092746 A1 | 4/2018 | Donno et al. |
| 2018/0125584 A1 | 5/2018 | Lang |
| 2018/0140440 A1 | 5/2018 | Jackson et al. |

FOREIGN PATENT DOCUMENTS

| | | |
|---|---|---|
| CN | 101330883 A | 12/2008 |
| CN | 101522137 A | 9/2009 |
| CN | 101642394 A | 2/2010 |
| CN | 101658446 A | 3/2010 |
| CN | 101664347 A | 3/2010 |
| CN | 101669844 A | 3/2010 |
| CN | 101627930 A | 10/2010 |
| CN | 101879099 A | 11/2010 |
| CN | 101959475 A | 1/2011 |
| CN | 102006839 A | 4/2011 |
| CN | 102006840 A | 4/2011 |
| CN | 102076283 A | 5/2011 |
| CN | 101330883 B | 3/2013 |
| CN | 103118633 A | 5/2013 |
| CN | 103732186 A | 4/2014 |
| CN | 103732187 A | 4/2014 |
| CN | 103732188 A | 4/2014 |
| CN | 103747762 A | 4/2014 |
| CN | 20365764 | 6/2014 |
| CN | 103732188 B | 5/2016 |
| CN | 103732186 B | 9/2016 |
| CN | 106214293 A | 12/2016 |
| DE | 202007014128 U1 | 1/2008 |
| EP | 0303467 A2 | 2/1989 |
| EP | 0546726 A1 | 6/1993 |
| EP | 0376658 B1 | 6/1994 |
| EP | 0381352 B1 | 6/1994 |
| EP | 0722721 A1 | 7/1996 |
| EP | 0567705 B1 | 7/1997 |
| EP | 0993812 A2 | 4/2000 |
| EP | 1013232 A2 | 6/2000 |
| EP | 1285638 A2 | 2/2003 |
| EP | 1033117 B1 | 6/2004 |
| EP | 0975286 B1 | 8/2004 |
| EP | 1477142 A2 | 11/2004 |
| EP | 1477143 A1 | 11/2004 |
| EP | 1013232 B1 | 10/2005 |
| EP | 1285638 B1 | 11/2005 |
| EP | 1719478 A2 | 11/2006 |
| EP | 1722721 A1 | 11/2006 |
| EP | 1354571 B1 | 6/2007 |
| EP | 1862150 A1 | 12/2007 |
| EP | 2004099 A2 | 12/2008 |
| EP | 1867302 B1 | 9/2009 |
| EP | 2147660 A1 | 1/2010 |
| EP | 2158878 A1 | 3/2010 |
| EP | 1555962 B1 | 2/2011 |
| EP | 2324799 A2 | 5/2011 |
| EP | 2335654 A1 | 6/2011 |
| EP | 2720646 A1 | 4/2014 |
| FR | 2901996 A1 | 12/2007 |
| FR | 3008605 A1 | 1/2015 |
| JP | 64068255 A | 3/1989 |
| JP | 341694 Y2 | 9/1991 |
| JP | 3267055 A | 11/1991 |
| JP | 0553501 A | 3/1993 |
| JP | 0568987 A | 3/1993 |
| JP | 9149908 A | 6/1997 |
| JP | 11504226 A | 4/1999 |
| JP | 11511347 A | 10/1999 |
| JP | 2003513706 A | 4/2003 |
| JP | 3469972 B2 | 11/2003 |
| JP | 3495161 B2 | 2/2004 |
| JP | 2004166802 A | 6/2004 |
| JP | 2005532089 A | 10/2005 |
| JP | 2008502393 A | 1/2008 |
| JP | 2008503327 A | 2/2008 |
| JP | 4077041 B2 | 4/2008 |
| JP | 2008523962 A | 7/2008 |
| JP | 2009519781 A | 5/2009 |
| JP | 4820547 B2 | 11/2011 |
| JP | 5571863 B1 | 7/2014 |
| JP | 2014522290 A | 9/2014 |
| JP | 2014522291 A | 9/2014 |
| JP | 2014522292 A | 9/2014 |
| JP | 2014522671 A | 9/2014 |
| JP | 2015164599 A | 9/2015 |
| JP | 5792898 B2 | 10/2015 |
| WO | WO-9014806 A1 | 12/1990 |
| WO | WO-9535074 A1 | 12/1995 |
| WO | WO-9603939 A1 | 2/1996 |
| WO | WO-0023010 A1 | 4/2000 |
| WO | WO-03094782 A2 | 11/2003 |
| WO | WO-2004016204 A1 | 2/2004 |
| WO | WO-2004084740 A1 | 10/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2007007841 A1 | 1/2007 |
| WO | WO-2007053905 A1 | 5/2007 |
| WO | WO-2007054553 A1 | 5/2007 |
| WO | WO-2007070859 A2 | 6/2007 |
| WO | WO-2007109641 A2 | 9/2007 |
| WO | WO-2008054389 A1 | 5/2008 |
| WO | WO-2009088234 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010008803 A2 | 1/2010 |
| WO | WO-2010075365 A2 | 7/2010 |
| WO | WO-2010108550 A2 | 9/2010 |
| WO | WO-2011072235 A2 | 6/2011 |

(56) References Cited

FOREIGN PATENT DOCUMENTS

| WO | WO-2012031774 A1 | 3/2012 |
|---|---|---|
| WO | WO-2012112698 A2 | 8/2012 |
| WO | WO-2012173704 A1 | 12/2012 |
| WO | WO-2012173706 A1 | 12/2012 |
| WO | WO-2012173740 A1 | 12/2012 |
| WO | WO-2016153927 A1 | 9/2016 |
| WO | WO-2017058535 A1 | 4/2017 |

OTHER PUBLICATIONS

"U.S. Appl. No. 12/974,018, Appeal Decision mailed Aug. 1, 2017", 8 pgs.
"U.S. Appl. No. 14/809,810, Non Final Office Action dated Sep. 29, 2017", 9 pgs.
"U.S. Appl. No. 14/809,810, Response filed Dec. 27, 2017 to Non Final Office Action dated Sep. 29, 2017", 14 pgs.
"U.S. Appl. No. 14/845,522, Final Office Action dated Jun. 13, 2017", 6 pgs.
"U.S. Appl. No. 14/845,522, Final Office Action dated Oct. 18, 2016", 10 pgs.
"U.S. Appl. No. 14/845,522, Non Final Office Action dated Feb. 8, 2017", 11 pgs.
"U.S. Appl. No. 14/845,522, Notice of Allowance dated Sep. 14, 2017", 7 pgs.
"U.S. Appl. No. 14/845,522, Response filed Apr. 12, 2017 to Non Final Office Action dated Feb. 8, 2017", 16 pgs.
"U.S. Appl. No. 14/845,522, Response filed Aug. 14, 2017 to Final Office Action dated Jun. 13, 107", 14 pgs.
"U.S. Appl. No. 14/845,622, Response filed Jan. 11, 2017 to Final Office Action dated Oct. 18, 2016", 12 pgs.
"U.S. Appl. No. 15/092,107, Restriction Requirement dated Nov. 17, 2017", 7 pgs.
"U.S. Appl. No. 15/424,382, Preliminary Amendment filed Feb. 23, 2017", 9 pgs.
"U.S. Appl. No. 15/835,144, Preliminary Amendment filed Dec. 27, 2017", 7 pgs.
"Australian Application Serial No. 2016202865, First Examination Report dated Jun. 26, 2017", 2 pgs.
"Australian Application Serial No. 2016202865, Response filed Aug. 16, 2017 to First Examination Report dated Sep. 26, 2017", 22pgs.
"Chinese Application Serial No. 201610697089.0, Office Action dated Jul. 25, 2017", With English Translation, 30 pgs.
"Chinese Application Serial No. 201610697089.0, Response filed Nov. 1, 2017 to Office Action dated Jul. 25, 2017", w/English Claims, 11 pgs.
"European Application Serial No. 14200265.8, Response Filed on Mar. 21, 2017 to Extended European Search Report dated Aug. 22, 2016", 18 pgs.
"International Application Serial No. PCT/US2016/022907, International Preliminary Report on Patentability dated Oct. 5, 2017", 9 pgs.
"International Application Serial No. PCT/US2016/052173, International Search Report dated Jan. 10, 2017", 6 pgs.
"International Application Serial No. PCT/US2016/052173, Written Opinion dated Jan. 10, 2017", 7 pgs.
"Natural-Knee® Modular Cemented Baseplate", [Online] retrieved from the internet:URL:http://www.zimmer.com/content/dam/zimmer-web/documents/en-US/pdf/medical-professionals/knee/natural-knee-modular-cemented-baseplate-brochure.pdf, (2004), 4 pgs.
"Answer filed Dec. 1, 2010 of Zimmer, Inc and Zimmer Technology, Inc", *W. Norman Scott and Giles R Scuderi* vs. *Zimmer, Inc and Zimmer Technology, Inc.* in the US District Court of Delaware in Case No. 10-772-GMS, (Dec. 1, 2010), 36 pgs.
"U.S. Appl. No. 11/611,021, Advisory Action dated Jan. 22, 2016", 3 pgs.
"U.S. Appl. No. 11/611,021, Examiner Interview Summary dated Jun. 30, 2016", 3 pgs.
"U.S. Appl. No. 11/611,021, Final Office Action dated Mar. 10, 2011", 7 pgs.
"U.S. Appl. No. 11/611,021, Final Office Action dated Sep. 25, 2014", 9 pgs.
"U.S. Appl. No. 11/611,021, Final Office Action dated Nov. 6, 2015", 11 pgs.
"U.S. Appl. No. 11/611,021, Non Final Office Action dated Jan. 17, 2014", 11 pgs.
"U.S. Appl. No. 11/611,021, Non Final Office Action dated Apr. 8, 2016", 11 pgs.
"U.S. Appl. No. 11/611,021, Non Final Office Action dated Jun. 17, 2015", 12 pgs.
"U.S. Appl. No. 11/611,021, Non Final Office Action dated Jul. 21, 2010", 8 pgs.
"U.S. Appl. No. 11/611,021, Non-Final Office Action dated Dec. 7, 2009", 4 pgs.
"U.S. Appl. No. 11/611,021, Preliminary Amendment filed Oct. 26, 2007", 7 pgs.
"U.S. Appl. No. 11/611,021, Response filed Jan. 4, 2016 to Final Office Action dated Nov. 6, 2015", 12 pgs.
"U.S. Appl. No. 11/611,021, Response filed Feb. 24, 2015 to Final Offce Action dated Sep. 25, 2014", 16 pgs.
"U.S. Appl. No. 11/611,021, Response filed May 3, 2010 to Non Final Office Action dated Dec. 7, 2009", 14 pgs.
"U.S. Appl. No. 11/611,021, Response filed Jun. 6, 2011 Final Office Action dated Mar. 10, 2011", 8 pgs.
"U.S. Appl. No. 11/611,021, Response filed Jul. 15, 2014 to Non-Final Office Action dated Jan. 17, 2014", 19 pgs.
"U.S. Appl. No. 11/611,021, Response filed Aug. 5, 2016 to Non Final Office Action dated Apr. 8, 2016", 18 pgs.
"U.S. Appl. No. 11/611,021, Response filed Aug. 25, 2015 to Non Final Office Action dated Aug. 17, 2015", 14 pgs.
"U.S. Appl. No. 11/611,021, Response filed Dec. 21, 2010 to Non Final Office Action dated Jul. 21, 2010", 14 pgs.
"U.S. Appl. No. 11/780,248, Non Final Office Action dated Feb. 4. 2010", 4 pgs.
"U.S. Appl. No. 11/780,248, Non Final Office Action dated Jul. 21, 2010", 11 pgs.
"U.S. Appl. No. 11/780,248, Response filed May 3, 2010 to Non Final Office Action dated Feb. 4, 2010", 13 pgs.
"U.S. Appl. No. 12/974,018, Appeal Brief filed Feb. 20, 2015", 24 pgs.
"U.S. Appl. No. 12/974,018, Final Office Action dated Apr. 13, 2012", 11 pgs.
"U.S. Appl. No. 12/974,018, Final Office Action dated Oct. 10, 2014", 12 pgs.
"U.S. Appl. No. 12/974,018, Non Final Office Action dated Apr. 4, 2014", 11 pgs.
"U.S. Appl. No. 12/974,018, Non Final Office Action dated Nov. 10, 2011", 5 pgs.
"U.S. Appl. No. 12/974,018, Preliminary Amendment filed Dec. 21, 2010", 4 pgs.
"U.S. Appl. No. 12/974,018, Response filed Mar. 8, 2012 to Non Final Office Action dated Nov. 10, 2011", 12 pgs.
"U.S. Appl. No. 12/974,018, Response filed Jul. 30, 2014 to Non-Final Office Action dated Apr. 4, 2014", 15 pgs.
"U.S. Appl. No. 12/974,018, Response filed Oct. 12, 2012 to Final Office Action dated Apr. 13, 2012", 16 pgs.
"U.S. Appl. No. 13/161,624, Notice of Allowance dated Mar. 12, 2013", 11 pgs.
"U.S. Appl. No. 13/161,624, Response filed Feb. 26, 2013 to Restriction Requirement dated Sep. 26, 2012", 9 pgs.
"U.S. Appl. No. 13/161,624, Restriction Requirement dated Sep. 26, 2012", 8 pgs.
"U.S. Appl. No. 13/459,060, Advisory Action dated Jun. 8, 2015", 3 pgs.
"U.S. Appl. No. 13/459,060, Final Office Action dated Apr. 1, 2015", 11 pgs.
"U.S. Appl. No. 13/459,060, Non Final Office Action dated Mar. 14, 2014", 8 pgs.
"U.S. Appl. No. 13/459,060, Non Final Office Action dated Oct. 9, 2014", 11 pgs.

(56) References Cited

OTHER PUBLICATIONS

"U.S. Appl. No. 13/459,060, Notice of Allowance dated Dec. 7, 2015", 7 pgs.
"U.S. Appl. No. 13/459,060, Preliminary Amendment filed Apr. 27, 2012", 6 pgs.
"U.S. Appl. No. 13/459,060, PTO Response to Rule 312 Communication dated Mar. 3, 2016", 2 pgs.
"U.S. Appl. No. 13/459,060, Response filed Jan. 3, 2014 to Restriction Requirement dated Nov. 4, 2013", 25 pgs.
"U.S. Appl. No. 13/459,060, Response filed Feb. 18, 2015 to Non-Final Office Action dated Oct. 9, 2014", 23 pgs.
"U.S. Appl. No. 13/459,060, Response filed May 28, 2015 to Final Office Action dated Apr. 1, 2015", 21 pgs.
"U.S. Appl. No. 13/459,060, Response filed Jul. 14, 2014 to Non-Final Office Action dated Mar. 14, 2014", 30 pgs.
"U.S. Appl. No. 13/459,060, Restriction Requirement dated Nov. 4, 2013", 6 pgs.
"U.S. Appl. No. 13/459,061, Advisory Action dated Sep. 30, 2014", 3 pgs.
"U.S. Appl. No. 13/459,061, Final Office Action dated Jul. 23, 2014", 10 pgs.
"U.S. Appl. No. 13/459,061, Non Final Office Action dated Mar. 26, 2014", 8 pgs.
"U.S. Appl. No. 13/459,061, Non Final Office Action dated Nov. 10, 2014", 9 pgs.
"U.S. Appl. No. 13/459,061, Notice of Allowance dated Feb. 27, 2015", 8 pgs.
"U.S. Appl. No. 13/459,061, Preliminary Amendment filed Apr. 27, 2012", 6 pgs.
"U.S. Appl. No. 13/459,061, Response filed Jan. 10, 2014 to Restriction Requirement dated Nov. 12, 2013", 8 pgs.
"U.S. Appl. No. 13/459,061, Response filed Feb. 10, 2015 to Non Final Office Action dated Nov. 10, 2014", 12 pgs.
"U.S. Appl. No. 13/459,061, Response filed Jun. 25, 2014 to Non Final Office Action dated Mar. 26, 2014", 11 pgs.
"U.S. Appl. No. 13/459,061, Response filed Sep. 19, 2014 to Final Office Action dated Jul. 23, 2014", 9 pgs.
"U.S. Appl. No. 13/459,061, Restriction Requirement dated Nov. 12, 2013", 5 pgs.
"U.S. Appl. No. 13/459,064, Final Office Action dated Jun. 13, 2014", 10 pgs.
"U.S. Appl. No. 13/459,064, Non Final Office Action dated Mar. 6, 2014", 8 pgs.
"U.S. Appl. No. 13/459,064, Notice of Allowance dated Aug. 28, 2014", 8 pgs.
"U.S. Appl. No. 13/459,064, Preliminary Amendment filed Apr. 27, 2012", 6 pgs.
"U.S. Appl. No. 13/459,064, PTO Response to Rule 312 Communication dated Dec. 15, 2014", 2 pgs.
"U.S. Appl. No. 13/459,064, Response filed Jan. 27, 2014 to Restriction Requirement dated Nov. 25, 2013", 13 pgs.
"U.S. Appl. No. 13/459,064, Response filed Jun. 3, 2014 to Non-Final Office action dated Mar. 6, 2014", 13 pgs.
"U.S. Appl. No. 13/459,064, Response filed Aug. 13, 2014 to Final Office Action dated Jun. 13, 2014", 13 pgs.
"U.S. Appl. No. 13/459,064, Restriction Requirement dated Nov. 25, 2013", 5 pgs.
"U.S. Appl. No. 13/819,528, Advisory Action dated Apr. 14, 2015", 3 pgs.
"U.S. Appl. No. 13/819,528, Final Office Action dated Feb. 5, 2015", 15 pgs.
"U.S. Appl. No. 13/819,528, Non Final Office Action dated Aug. 12, 2014", 10 pgs.
"U.S. Appl. No. 13/819,528, Non Final Office Action mailed Dec. 6, 2013", 15 pgs.
"U.S. Appl. No. 13/819,528, Notice of Allowance dated Jun. 22, 2015", 7 pgs.
"U.S. Appl. No. 13/819,528, Preliminary Amendment filed Feb. 27, 2013", 9 pgs.
"U.S. Appl. No. 13/819,528, Response filed Jan. 12, 2015 to Non Final Office Action dated Aug. 12, 2014", 13 pgs.
"U.S. Appl. No. 13/819,528, Response filed Apr. 2, 2015 to Final Office Action dated Feb. 5, 2015", 12 pgs.
"U.S. Appl. No. 13/819,528, Response filed Apr. 29, 2015 to Advisory Action dated Apr. 14, 2015", 13 pgs.
"U.S. Appl. No. 13/819,528, Response filed May 22, 2014 to Non Final Office Action dated Dec. 6, 2013", 15 pgs.
"U.S. Appl. No. 13/819,528, Supplemental Preliminary Amendment filed Jul. 11, 2013", 6 pgs.
"U.S. Appl. No. 14/014,737, Advisory Action dated Oct. 23, 2014", 3 pgs.
"U.S. Appl. No. 14/014,737, Appeal Brief filed Feb. 12, 2015", 12 pgs.
"U.S. Appl. No. 14/014,737, Final Office Action dated Aug. 15, 2014", 5 pgs.
"U.S. Appl. No. 14/014,737, Non Final Office Action dated May 6, 2014", 6 pgs.
"U.S. Appl. No. 14/014,737, Pre-Appeal Brief Request filed Nov. 14, 2014", 4 pgs.
"U.S. Appl. No. 14/014,737, Preliminary Amendment filed Nov. 6, 2013", 7 pgs.
"U.S. Appl. No. 14/014,737, Response filed Aug. 6, 2014 to Non-Final Office Action dated May 6, 2014", 8 pgs.
"U.S. Appl. No. 14/014,737, Response filed Oct. 15, 2014 to Final Office Action dated Aug. 15, 2014", 8 pgs.
"U.S. Appl. No. 14/525,595, Application filed Oct. 28, 2014", 40 pgs.
"U.S. Appl. No. 14/553,034, Non Final Office Action dated Apr. 20, 2016", 15 pgs.
"U.S. Appl. No. 14/553,034, Preliminary Amendment filed Mar. 13, 2015", 10 pgs.
"U.S. Appl. No. 14/553,034, Response filed Aug. 22, 2016 to Non Final Office Action dated Apr. 20, 2016", 10 pgs.
"U.S. Appl. No. 14/731,013, Supplemental Preliminary Amendment filed Jun. 18, 2015", 5 pgs.
"U.S. Appl. No. 14/845,522, Non Final Office Action dated Jun. 1, 2016", 11 pgs.
"U.S. Appl. No. 14/845,522, Preliminary Amendment filed Sep. 24, 2015", 7 pgs.
"U.S. Appl. No. 14/845,522, Response filed Sep. 1, 2016 to Non Final Office Action dated Jun. 1, 2016", 14 pgs.
"U.S. Appl. No. 15/092,107, Preliminary Amendment filed Apr. 7, 2016", 11 pgs.
"U.S. Appl. No. 61/381,803, Application filed Sep. 10, 2010", 23 pgs.
"Australian Application Serial No. 2006325787, Office Action dated Mar. 14, 2012", 2 pgs.
"Australian Application Serial No. 2006325787, Office Action dated Nov. 14, 2011", 2 pgs.
"Australian Application Serial No. 2006325787, Response filed May 3, 2013 to Office Action dated Mar. 14, 2012", 10 pgs.
"Australian Application Serial No. 2006325787, Response filed Feb. 21, 2012 to Office Action dated Nov. 14, 2011", 34 pgs.
"Australian Application Serial No. 2012271153, Amendment filed Jan. 16, 2014", 13 pgs.
"Australian Application Serial No. 2012271186, First Examiner Report dated Dec. 15, 2015", 3 pgs.
"Australian Application Serial No. 2012271186, Response filed Jun. 24, 2016 to First Examiner Report dated Dec. 15, 2015", 14 pgs.
"Australian Application Serial No. 2012271186, Subsequent Examiners Report dated Aug. 2, 2016", 3 pgs.
"Australian Application Serial No. 2012271243, Subsequent Examiners Report dated Apr. 13, 2015", 2 pgs.
"Australian Application Serial No. 2012271244, First Examiner Report dated Dec. 15, 2015", 3 pgs.
"Australian Application Serial No. 2012271244, Response filed Jun. 24, 2016 to First Examiner Report dated Dec. 15, 2015", 13 pgs.
"Australian Application Serial No. 2013245552, First Examiner Report dated Mar. 30, 2016", 4 pgs.
"Canadian Application Serial No. 2,641.966, Office Action dated Feb. 6, 2014", 2 pgs.

(56) References Cited

OTHER PUBLICATIONS

"Canadian Application Serial No. 2,641,966, Office Action dated Jul. 16, 2013"; 2 pgs.
"Canadian Application Serial No. 2,641,966, Office Action dated Aug. 25, 2014", 2 pgs.
"Canadian Application Serial No. 2,641,966, Office Action dated Sep. 4, 2015", 4 pgs.
"Canadian Application Serial No. 2,641,966, Response filed Jan. 15, 2014 to Office Action dated Jul. 16, 2013", 6 pgs.
"Canadian Application Serial No. 2,641,966, Response filed Feb. 25, 2015 to Office Action dated Aug. 25, 2014", 4 pgs.
"Canadian Application Serial No. 2,641;966, Response filed Aug. 6, 2014 to Office Action dated Feb. 6, 2014", 3 pgs.
"Chinese Application Serial No. 200680046893, Office Action dated Aug. 3, 2012", (W/ English Translation), 8 pgs.
"Chinese Application Serial No. 200680046893, Office Action dated Aug. 10, 2010", (W/ English Translation), 22 pgs.
"Chinese Application Serial No. 200680046893, Office Action dated Dec. 6, 2011", (W/ English Translation), 5 pgs.
"Chinese Application Serial No. 200680046893, Response filed Jan. 23, 2012 to Office Action dated Dec. 6, 2011", (W/ English Translation), 11 pgs.
"Chinese Application Serial No. 200680046893.7, Response filed Oct. 17, 2012 to Office Action dated Aug. 3, 2012", (W/ English Translation), 8 pgs.
"Chinese Application Serial No. 201280039703.4, Office Action dated Mar. 30, 2015", (W/ English Translation), 2 pgs.
"Chinese Application Serial No. 201280039703.4, Office Action dated May 10, 2016", No English Translation, 3 pgs.
"Chinese Application Serial No. 201280039703.4, Office Action dated May 28, 2015", (W/ English Translation), 12 pgs.
"Chinese Application Serial No. 201280039703.4, Office Action dated Dec. 3, 2015", No English Translation, 3 pgs.
"Chinese Application Serial No. 201280039703.4, Response filed Feb. 1, 2016 to Office Action dated Dec. 3, 2015", No English Translation, 12 pgs.
"Chinese Application Serial No. 201280039703.4, Response filed May 31, 2016 to Office Action dated May 10, 2016", (W/ English Translation), 34 pgs.
"Chinese Application Serial No. 201280039703.4, Response filed Sep. 7, 2015 to Office Action dated May 28, 2015", (W/ English Translation), 72 pgs.
"Chinese Application Serial No. 201280039705.3, Office Action dated Mar. 20, 2015", (W/ English Translation), 15 pgs.
"Chinese Application Serial No. 201280039705.3, Response filed Aug. 6, 2015 to Office Action dated Mar. 20, 2015", (W/ English translation of claims), 11 pgs.
"Chinese Application Serial No. 201280039705.3, Voluntary Amendment filed Jul. 22, 2014"; No English Translation, 5 pgs.
"Chinese Application Serial No. 201280039706.8, Office Action dated Feb. 26, 2016", W/ English Translation, 4 pgs.
"Chinese Application Serial No. 201280039706.8, Office Action dated May 19, 2015", (W/ English Translation), 14 pgs.
"Chinese Application Serial No. 201280039706.8, Response filed May 11, 2016 to Office Action dated Feb. 26, 2016", W/ English Translation of Claims, 9 pgs.
"Chinese Application Serial No. 201280039706.8, Response filed Nov. 16, 2015 to Office Action dated May 19, 2015", W/ English Translation of Claims, 16 pgs.
"Chinese Application Serial No. 201280039714.2, Office Action dated May 4, 2015", (W/ English Translation), 19 pgs.
"Chinese Application Serial No. 201280039714.2, Office Action dated Dec. 3, 2015", (W/ English Translation), 7 pgs.
"Chinese Application Serial No. 201280039714.2, Response filed Feb. 1, 2016 to Office Action dated Dec. 3, 2015", No English Translation, 5 pgs.
"Chinese Application Serial No. 201280039714.2, Response filed Sep. 18, 2015 to Office Action dated May 4, 2015", (W/ English Translation of Claims), 9 pgs.

"Complaint of W. Norman Scot and Giles R. Scuderi filed Sep. 9, 2010", *W. Norman Scott and Giles R Scuderi* vs. *Zimmer, Inc and Zimmer Technology, Inc* in the US District Court of Delaware in Case No. 10-772-GMS, (Sep. 9, 2010), 24 pgs.
"European Application Serial No. 06840269.2, Decision to Grant dated Feb. 18, 2016", 3 pgs.
"European Application Serial No. 06840269.2, Examination Notification Art. 94(3) dated Jan. 24, 2014", 6 pgs.
"European Application Serial No. 06840269.2, Examination Notification Art. 94(3) dated Nov. 12, 2014", 4 pgs.
"European Application Serial No. 06840269.2, Office Action dated Sep. 8, 2015", 67 pgs.
"European Application Serial No. 06840269.2, Response filed Mar. 23, 2015 to Examination Notification Art. 94(3) dated Nov. 12, 2014", 10 pgs.
"European Application Serial No. 06840269.2, Response filed Aug. 4, 2014 to Examination Notification Art. 94(3) dated Jan. 24, 2014", 10 pgs.
"European Application Serial No. 12720354.5, Decision of Grant dated Dec. 3, 2015", 3 pgs.
"European Application Serial No. 12720354.5, Examination Notification Art. 94(3) dated Oct. 22, 2014", 4 pgs.
"European Application Serial No. 12720354.5, Office Action dated Jun. 17, 2015", 96 pgs.
"European Application Serial No. 12720354.5, Response filed Aug. 21, 2014 to Communication pursuant to Rules 161(2) and 162 EPC dated Feb. 14, 2014", 17 pgs.
"European Application Serial No. 12720354.5, Response filed Dec. 24, 2014 to Examination Notification Art. 94(3) dated Oct. 22, 2014", 13 pgs.
"European Application Serial No. 12722967.2, Examination Notification Art. 94(3) dated Oct. 22, 2014", 4 pgs.
"European Application Serial No. 12724484.6, Communication Pursuant to Article 94(3) EPC dated May 2, 2016", 5 pgs.
"European Application Serial No. 12724484.6, Examination Notification Art. 94(3) dated Dec. 3, 2014", 5 pgs.
"European Application Serial No. 12724484.6, Response filed Apr. 13, 2015 to Examination Notification Art. 94(3) dated Dec. 3, 2014", 16 pgs.
"European Application Serial No. 12724484.6, Response filed Aug. 20, 2014 to Communication pursuant to Rules 161(1) and 162 EPC dated Feb. 14, 2014", 10 pgs.
"European Application Serial No. 14200265.8, Extended European Search Report dated Aug. 22, 2016", 23 pgs.
"European Application Serial No. 15180629.6, Extended European Search Report dated Aug. 24, 2016", 8 pgs.
"Gender Solutions Natural-Knee Flex System", Zimmer, Inc., (2007, 2009), 6 pgs.
"Gender Solutions Natural-Knee Flex System: Surgical Technique", Zimmer, Inc., (2007, 2008, 2009), 36 pgs.
"Gender Solutions Patello-Femoral Joint (PFJ) System: Surgical Technique", Zimmer Inc., (2008, 2009), 38 pgs.
"International Application Serial No. PCT/EP2011/004556, International Preliminary Report on Patentability dated Mar. 12, 2013", 9 pgs.
"International Application Serial No. PCT/EP2011/004556, International Search Report dated Feb. 9, 2012", 6 pgs.
"International Application Serial No. PCT/EP2011/004556, Written Opinion dated Mar. 12, 2013", 9 pgs.
"international Application Serial No. PCT/US2006/062117, International Preliminary Report on Patentability dated Jun. 18, 2008", 5 pgs.
"International Application Serial No. PCT/US2006/062117, Written Opinion dated Apr. 5, 2007", 4 pgs.
"International Application Serial No. PCT/US2012/035688, International Preliminary Report on Patentability dated Jan. 3, 2014", 13 pgs.
"International Application Serial No. PCT/US2012/035688, Partial Search Report dated Jul. 3, 2012", 8 pgs.
"International Application Serial No. PCT/US2012/035688, Search Report dated Sep. 17, 2012", 7 pgs.
"International Application Serial No. PCT/US2012/035688, Written Opinion dated Sep. 17, 2012", 11 pgs.

(56) References Cited

OTHER PUBLICATIONS

"International Application U.S. Appl. No. PCT/US2012/035691, International Preliminary Report on Patentability dated Jan. 3, 2014", 13 pgs.
"International Application U.S. Appl. No. PCT/US2012/035691, Partial Search Report dated Jul. 10, 2012", 8 pgs.
"International Application Serial No. PCT/US2012/035691, Search Report dated Sep. 17, 2012", 7 pgs.
"International Application Serial No. PCT/US2012/035691, Written Opinion dated Sep. 17, 2012", 11 pgs.
"International Application Serial No. PCT/US2012/035693, International Preliminary Report on Patentability dated Jan. 3, 2014", 13 pgs.
"International Application Serial No. PCT/US2012/035693, Partial Search Report dated Jun. 27, 2012", 8 pgs.
"International Application Serial No. PCT/US2012/035693, Search Report dated Oct. 9, 2012", 7 pgs.
"International Application Serial No. PCT/US2012/035693 Written Opinion dated Oct. 9, 2012", 11 pgs.
"International Application Serial No. PCT/US2012/038531, International Preliminary Report on Patentability dated Jan. 3, 2014", 12 pgs.
"International Application Serial No. PCT/US2012/038531, International Search Report dated Oct. 8, 2012", 14 pgs.
"International Application Serial No. PCT/US2012/038531, Written Opinion dated Oct. 8, 2012", 10 pgs.
"International Application Serial No. PCT/US2016/022907, International Search Report dated Jul. 7, 2016", 7 pgs.
"International Application Serial No. PCT/US2016/022907, Written Opinion dated Jul. 7, 2016", 13 pgs.
"Japanese Application Serial No. 2008-545981, Examiners Decision of Final Refusal dated Oct. 16, 2012", (W/ English Translation), 3 pgs.
"Japanese Application Serial No. 2008-545981, Office Action dated Apr. 17, 2012", (W/ English Translation), 5 pgs.
"Japanese Application Serial No. 2008-545981, Office Action dated Jul. 5, 2011", (W/ English Translation), 13 pgs.
"Japanese Application Serial No. 2008-545981, Response filed Oct. 5, 2011 to Office Action dated Jul. 5, 2011", (W/ English Translation), 6 pgs.
"Japanese Application Serial No. 2008-545981, Response filed Aug. 30, 2012 to Office Action dated Apr. 17, 2012", (W/ English Translation), 5 pgs.
"Japanese Application Serial No. 2011-221305, Office Action dated Feb. 26, 2013", (W/ English Translation), 13 pgs.
"Japanese Application Serial No. 2011-221305, Office Action dated Sep. 17, 2013", (W/ English Translation), 5 pgs.
"Japanese Application Serial No. 2011-221305, Response filed Aug. 26, 2013 to Office Action dated Feb. 26, 2013", (W/ English Translation), 9 pgs.
"Japanese Application Serial No. 2011-221305, Response filed Dec. 17, 2013 to Office Action dated Sep. 17, 2013", (W/ English Translation of Claims), 8 pgs.
"Japanese Application Serial No. 2014-515819, Notice of Allowance dated Dec. 15, 2015", (W/ English Translation), 13 pgs.
"Japanese Application Serial No. 2014-515819, Office Action dated Feb. 3, 2015", (W/ English Translation), 15 pgs.
"Japanese Application Serial No. 2014-515819, Response filed Jul. 29, 2015 to Office Action dated Feb. 3, 2015", (W/ English translation of claims), 11 pgs.
"Japanese Application Serial No. 2014-515820, Office Action dated Dec. 2, 2014", (W/ English Translation), 8 pgs.
"Japanese Application Serial No. 2014-515821, Request for Examination Amendment filed Apr. 8, 2014", (W/ English Translation), 18 pgs.
"Japanese Application Serial No. 2014-515831, Office Action dated Dec. 16, 2014", (W/ English Translation), 12 pgs.
"Japanese Application Serial No. 2015-124808, Amendment filed Jul. 16, 2015", (W/ English Translation), 8 pgs.
"Japanese Application Serial No. 2015-124808, Office Action dated Jun. 7, 2016", (W/ English Translation), 5 pgs.
"LPS-Flex Fixed Bearing Knee: Surgical Technique", Zimmer, Inc., (2004, 2007, 2008), 1 pgs.
"Nexgen Complete Knee Solution", Extrarnalullary/Intramedullary Tibial Resector: Surgical Technique, Zimmer, Inc. 97-5997-02 Rev 1, (2000), 26 pgs.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"Surgical Technique for the CR-Flex Fixed Bearing Knee", NexGen Complete Knee Solution, Zimmer, Inc., (2003), 22 pgs.
"Unicompartmental High Flex Knee: Intramedullary, Spacer Block Option and Extramedullary Minimally Invasive Surgical Techniques", Zimmer, Inc., (2004, 2009, 2010), 62 pgs.
Hitt, Kirby, et al., "Anthropometric Measurements of the Human Knee: Correlation to the Sizing of Current Knee Arthroplasty Systems", The Journal of Bone & Joint Surgery. (2003), 114-122.
Mensch, Joseph S, et al., "Knee Morphology as a Guide to Knee Replacement", Clinical Orthopaedics and Related Research No. 112, (Oct. 1975), 231-241.
Poilvache, Pascal L, et al., "Rotational Landmarks and Sizing of the Distal Femur in Total Knee Arthroplasty", Clinical Orthopaedics and Related Research, No. 331. (1996), 35-46.
Seedhom, B B, et al., "Dimensions of the Knee—Radiographic and Autopsy Study of Sizes Required for a Knee Prosthesis", Annals of the Rheumatic Diseases, (1972), 54-58.
Yoshioka, Yuki, et al., "The Anatomy and Functional Axes of the Femur", The Journal of Bone and Joint Surgery, vol. 69A, No. 6, (Jul. 1987), 873-880.
"U.S. Appl. No. 15/092,107, Response filed Jan. 9, 2018 to Restriction Requirement dated Nov. 17, 2017", 16 pgs.
"U.S. Appl. No. 14/809,810, Advisory Action dated Jun. 27, 2018", 3 pgs.
"U.S. Appl. No. 14/809,810, Final Office Action dated May 2, 2018", 10 pgs.
"U.S. Appl. No. 14/809,810, Response filed Jun. 15, 2018 to Final Office Action dated May 2, 2018", 14 pgs.
"U.S. Appl. No. 15/092,107, Notice of Allowability dated Apr. 18, 2018", 2 pgs.
"U.S. Appl. No. 15/092,107, Notice of Allowance dated Apr. 18, 2018", 8 pgs.
"International Application Serial No. PCT/US2016/052173, International Preliminary Report on Patentability dated Apr. 12, 2018", 8 pgs.
"Chinese Application Serial No. 201610697089.0, Office Action dated Feb. 7, 2018", (W English Translation), 27 pgs.
"Canadian Application Serial No. 2,839,433, Office Action dated Feb. 26, 2018", 4 pgs.
"Chinese Application Serial No. 201610697089.0, Response filed Aug. 2, 2018 to Office Action dated Jul. 16, 2018", w o English translation, 10 pgs.
"Chinese Application Serial No. 201610697089.0, Office Action dated Jul. 16, 2018", w o English translation, 5 pgs.
"U.S. Appl. No. 15/835,144, Non Final Office Action dated Jul. 11, 2018", 9 pgs.

\* cited by examiner

TIBIAL PROSTHESIS FOR TIBIA WITH VARUS RESECTION

CLAIM OF PRIORITY

This application claims the benefit of U.S. Provisional Patent Application Ser. No. 62/234,141, filed on Sep. 29, 2015, the benefit of priority of which is claimed hereby, and which is incorporated by reference herein in its entirety.

FIELD

The present subject matter relates to orthopedic procedures and, more particularly, to tibial implants used in some knee arthroplasties where a varus resection of a tibia is utilized.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty (TKA), where all of the articulating compartments of the joint are repaired with prosthetic components.

OVERVIEW

The present inventor recognizes, among other things, an opportunity for reducing trauma to the lateral tibial metaphysis and/or lateral tibial diaphysis during a TKA. More particularly, the present inventor has recognized that traditional fixation members for the tibial component such as a stem, keel, and/or fins may not be appropriately referenced to a central axis of the intramedullary canal. A result of such misalignment is that the fixation member does not reference down the center of the intramedullary canal. This misalignment can result in the fixation member perforating the lateral metaphysis or lateral diaphysis when the tibial component is seated down into a position on top of the resected proximal end of the tibia. The present inventor proposes a tibial implant, methods, and systems where the fixation member is appropriately referenced to substantially align with the central axis of the intramedullary canal. Achieving this orientation can include having the fixation member(s) extend both distally and medially from a baseplate of the tibial implant such that the fixation member is oriented at an acute angle (i.e. be oriented in valgus) relative to the resected proximal surface (corresponding to a distal surface of a medial portion of the baseplate).

To further illustrate the apparatuses, systems and methods disclosed herein, the following non-limiting examples are provided:

In Example 1, a tibial implant configured for attachment to a tibia in a knee arthroplasty is disclosed. The tibial implant can be configured for attachment to a tibia in a knee arthroplasty and can include a baseplate having a lateral portion and a medial portion oriented relative to an anteroposterior axis and a fixation member. Each of the lateral portion and the medial portion can have a distal surface configured to interface with a resected proximal surface of a tibia. The fixation member can be coupled to and extend both distally and medially from the baseplate such that the fixation member is oriented at an acute angle relative to the distal surface of the medial portion.

In Example 2, the tibial implant of Example 1, wherein the fixation member can comprise one or both of a keel and a stem that are configured for insertion into a metaphysis and/or diaphysis of the tibia.

In Example 3, the tibial implant of Example 2, wherein one or both of the keel and stem can be configured to be removably attached to the baseplate.

In Example 4, the tibial implant of Example 3, wherein one or both of the keel and stem can be configured to be adjustable 180° relative to the baseplate such that the tibial implant can be configured for use with both a left tibia and a right tibia.

In Example 5, the tibial implant of Example 2, wherein the stem and keel can be configured to couple together, and wherein the stem can be configured to couple to the baseplate at the acute angle and coupling of the keel with the stem orients the keel at substantially a same acute angle relative to the distal surface of the medial portion as the acute angle.

In Example 6, the tibial implant of Example 2, wherein the stem and keel can be configured to couple together, and wherein the keel can be configured to couple to the baseplate at the acute angle and coupling of the stem with the keel orients the stem at substantially a same acute angle relative to the distal surface of the medial portion as the acute angle.

In Example 7, the tibial implant of any one or any combination of Examples 1-6, wherein the fixation member can include a symmetric feature having an axis of symmetry, and wherein the acute angle can be measured between the axis of symmetry and the distal surface of the medial portion.

In Example 8, the tibial implant of any one or any combination of Examples 1-7, wherein the fixation member can include a lateral portion and a medial portion, and wherein the medial portion has a greater surface area than the lateral portion.

In Example 9, the tibial implant of any one or any combination of Examples 1-8, wherein the baseplate and fixation member can be configured such that the fixation member is adjustable 180° relative to the baseplate such that the tibial implant is configured for use with both a left tibia and a right tibia.

In Example 10, a system for forming a tibial implant configured for attachment to a tibia in a knee arthroplasty is disclosed. The system can include one or more baseplates and a plurality of fixation members. The one or more baseplates can have a lateral portion and a medial portion oriented relative to an anteroposterior axis. Each of the lateral portion and the medial portion can have a distal surface configured to interface with a resected proximal surface of a tibia. Each of the plurality of fixation members can be configured to couple to the baseplate and can extend both distally and medially from the baseplate such that each fixation member of the plurality of fixation members is oriented at an acute angle relative to the distal surface of the medial portion. Each of the plurality of fixation members can be configured to differ from others of the plurality of fixation members such that the acute angle formed by each of the plurality of fixation members, when mounted to the baseplate, differs in degree.

In Example 11, the system of Example 10, wherein the plurality of fixation members can comprise a plurality of keels each having a different configuration and a single stem having a single configuration, wherein the single stem is configured to universally couple with any of the plurality of keels.

In Example 12, the system of Example 10, wherein the plurality of fixation members can comprise a plurality of stems each having a different configuration and a single keel having a single shape, wherein the single keel can be configured to universally couple with any of the plurality of stems.

In Example 13, the system of any one or any combination of Examples 10-12, wherein the baseplate and fixation member can be configured such that the fixation member can be coupled to the baseplate in at least two orientations including to create a first configuration for a right knee and a second configuration for a left knee.

In Example 14, a method of performing a knee arthroplasty is disclosed. The method can include resecting a proximal surface of a tibia to expose a tibial metaphysis, and attaching a tibial implant to the resected surface at a distal surface of a baseplate of the tibial implant, the tibial implant having a fixation member that is configured to generally align with a central axis of the tibial diaphysis when coupled to the distal surface of the baseplate.

In Example 15, the method of Example 14, can further comprise determining a desired angle based on degree of varus between the distal surface of the baseplate and the central axis of the tibial diaphysis, selecting from a plurality of fixation members that are configured to achieve the desired angle when coupled to the baseplate, and coupling the selected fixation member to the tibial baseplate.

In Example 16, the method of any one or any combination of Examples 14 and 15, wherein the plurality of fixation members can comprise a plurality of keels and a single stem configured to universally couple with all of the plurality of keels.

In Example 17, the method of any one or any combination of Examples 14 and 15, wherein the plurality of fixation members can comprise a plurality of stems and a single keel configured to universally couple with all of the plurality of stems.

In Example 18, a tibial implant configured for attachment to a tibia in a knee arthroplasty is disclosed. The tibial implant can include a baseplate, a keel, and a stem. The baseplate can have a lateral portion and a medial portion oriented relative to an anteroposterior axis, each of the lateral portion and the medial portion having a distal surface configured to interface with a resected proximal surface of a tibia. The keel can be coupled to and extending both distally and medially from the baseplate such that the keel creates an acute angle between the keel and the distal surface of the medial portion. The stem can be configured to couple with one or both of the keel and the baseplate and configured to removably insert within a receptacle of the keel to be oriented at the acute angle relative to the distal surface of the medial portion.

In Example 19, the tibial implant of Example 18, wherein the keel can comprise one of a plurality of keels each keel configured to form a different degree of acute angle when coupled to the baseplate.

In Example 20, the tibial implant of Example 18, wherein the stem can comprise one of a plurality of stems each stem configured to form a different degree of acute angle when coupled to the baseplate.

In Example 21, the tibial implant of any one or any combination of Examples 18-20, wherein the baseplate, keel, and stem are each configured such that at least one of the keel and stem is adjustable 180° relative to the baseplate such that the tibial implant is configured for use with both a left tibia and a right tibia.

In Example 22, the apparatuses or method of any one or any combination of Examples 1-21 can optionally be configured such that all elements or options recited are available to use or select from.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

It has been established that a kinematically aligned TKA can improve the results of the TKA, including overall patient satisfaction and mobility. Primary goals of kinematically aligned TKA are (1) positioning the femoral and tibial components of a knee prosthesis such that the angles and levels of the distal and posterior femoral and tibial joint lines are restored to the patient's natural joint line, (2) restoration of the patient's natural or constitutional alignment prior to the patient having developed osteoarthritis, and (3) restoration of the patient's natural soft tissue laxity and envelope. The kinematically aligned TKA can include a determination of three kinematic axes.

Figure 1A:
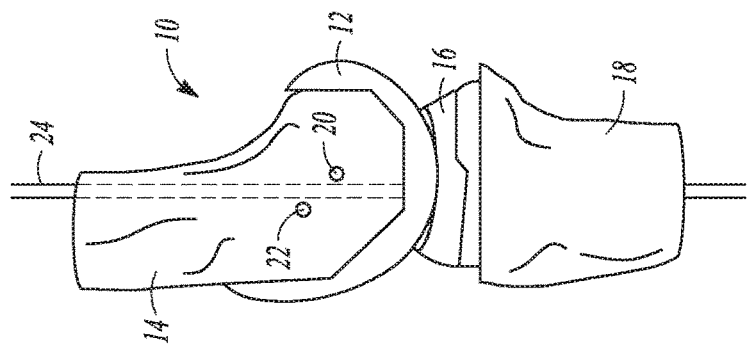
FIG. 1A is a frontal or coronal plane view of a knee joint with an implanted knee prosthesis according to an example of the present application.
Figure 1B:
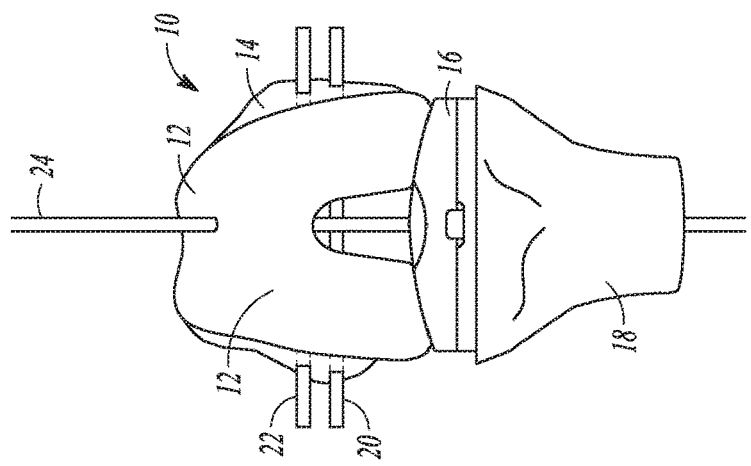
FIG. 1B is a coronal view of the knee joint and knee prosthesis of FIG. 1A in 90 degrees flexion according to an example of the present application.
Figure 1C:
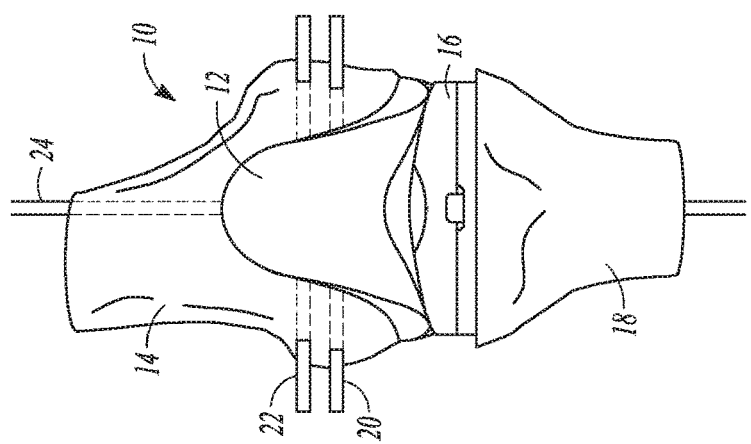
FIG. 1C is a side or sagittal plane view of the knee joint and knee prosthesis of FIGS. 1A and 1B in full extension according to an example of the present application.

FIGS. 1A-1C show various views of a knee prosthesis 10 implanted on a knee joint and illustrate the three kinematic axes of the knee joint in a kinematically aligned TKA. In particular, FIG. 1A provides a view of the knee prosthesis 10 in a coronal plane as viewed from the anterior with a femoral component 12 in extension. FIG. 1B is a view of the knee prosthesis 10 in the coronal plane with the femoral component 12 in flexion. FIG. 1C is a view of the 10 in the sagittal plane with the femoral component in extension. The femoral component 12 is implanted on a femur 14 while a tibial component 16 implanted on a tibia 18. A polyethylene surface is inserted between the femur and tibia. A first kinematic axis 20 can be a transverse axis in the femur 14 about which the tibia 18 flexes and extends. The first kinematic axis 20 can be determined by projecting the lateral and medial femoral condyles of the femur 14 onto one another and fitting circles of equal radii over each other. The first kinematic axis 20 passes through a center of the circles. A second kinematic axis 22 can be a second transverse axis, parallel to the first kinematic axis 20, about which a patella of the knee joint flexes and extends. The second kinematic axis 22 can be located anterior and proximal to the first kinematic axis 20. A third kinematic axis 24 is an axis perpendicular to the first 20 and second 22 axes about which the tibia 18 internally and externally rotates on the femur 14.

The present application does not include a description of the surgical procedure for performing a kinematically aligned TKA. Such procedures are discussed, for example, in relation to application Ser. No. 14/809,810, entitled "INSTRUMENTS AND METHODS IN PERFORMING KINEMATICALLY-ALIGNED TOTAL KNEE ARTHROPLASTY" filed Jul. 27, 2015, and Ser. No. 13/819,528, entitled "FEMORAL PROTHESIS WITH MEDIALIZED PATELLAR GROOVE", filed Sep. 9, 2011, the entire disclosures of which are incorporated herein by reference and are co-owned by the Applicant. Rather, FIGS. 2-7C provide examples of surgical instruments, systems, methods and techniques that can be used to aid and improve on the kinematically aligned TKA.

Figure 2:
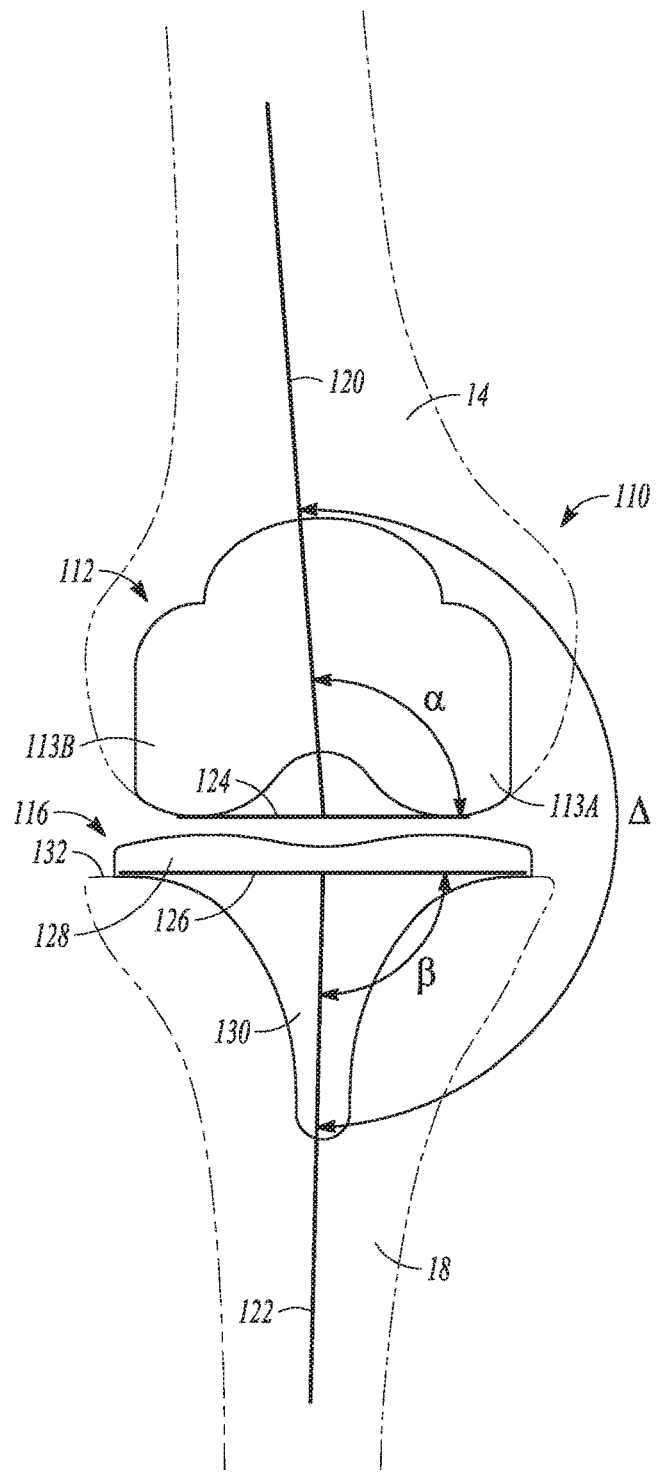
FIG. 2 is a coronal plane view of a tibia and a femur for a right knee having implants thereon and showing orientations of the implants relative to axes of the knee according to an example of the present application.

FIG. 2 shows an example of a TKA knee prosthesis 110 in a right knee of a patient as viewed in the coronal plane. As was generally discussed with respect to FIGS. 1A-1C, the knee prosthesis 110 can include a femoral component 112 mounted to the femur 14 and a tibial component 116 mounted to the tibia 18. FIG. 2 shows the knee prosthesis 110 alignment relative to the anatomical axes of the femur 14 and the tibia 18. In particular, FIG. 2 shows a femoral anatomical axis 120 and a tibial anatomical axis 122.

Disposition of the femoral component 112 relative to the femoral anatomical axis 120 is indicated by α as measured between a line 124 across the bottom of the femoral condyles 113A and 113B the femoral shaft axis (superimposed with the femoral anatomical axis 120). Disposition of the tibial component 116 relative to the tibial anatomical axis 122 is indicated by β as measured between a line 126 across a base of a tibial plate 128 of the tibial component 116 and a tibial shaft axis (superimposed with the tibial anatomical axis 122). An angle Δ (a tibiofemoral axis) is also indicated and comprises a measure between the femoral shaft axis and the tibial shaft axis.

An α of 90° comprises a neutral placement of the femoral component 112, α<90° corresponds to varus placement of the femoral component 112, and α>90° corresponds to valgus placement of the femoral component 112. Similarly, if (β=90° corresponds to a neutral placement of the tibial component 116, β<90° corresponds to varus placement of placement of the tibial component 116, and β>90° corresponds to valgus placement of the tibial component 116. If Δ=180° this corresponds to a neutral alignment, Δ<180° corresponds to varus alignment, and Δ>180° corresponds to valgus alignment.

With regard to coronal alignment of the femoral component 112, it has generally been shown that an optimal distal femoral cut is typically 2-7° of valgus. With regard to coronal alignment of the tibial component 116, a certain degree of varus tibial alignment with a varus cut is generally desirable. With the kinematically aligned TKA it has generally been found that tibial component 116 placement of a few more degrees varus (e.g., about 0.1 degrees to about 5 degrees) and the femoral component 112 placed in a few more degrees valgus (e.g., about 0.1 degrees to about 5 degrees) than traditional mechanically aligned TKA results in improved patient outcomes.

The present inventor has recognized that especially with the additional varus disposition of the tibial component 116 in the kinematically aligned TKA, traditional fixation members for the tibial component 116 such as a stem, keel, or fins (e.g, a keel and stem 130 as shown in FIG. 2) may not be appropriately referenced to the intramedullary canal which generally aligns with the tibial anatomical axis 122. Indeed, an example of such misalignment is shown in FIG. 2 where the keel 130 is not substantially aligned with the tibial anatomical axis 122. A result of such misalignment is that the keel 130 does not reference down the center of the tibial diaphysis/intramedullary canal. This misalignment can result in the keel 130 perforating the lateral metaphysis or lateral diaphysis when the tibial component 116 is seated down into a position on top of the resected proximal end surface 132 of the tibia 18.

Figure 3A:
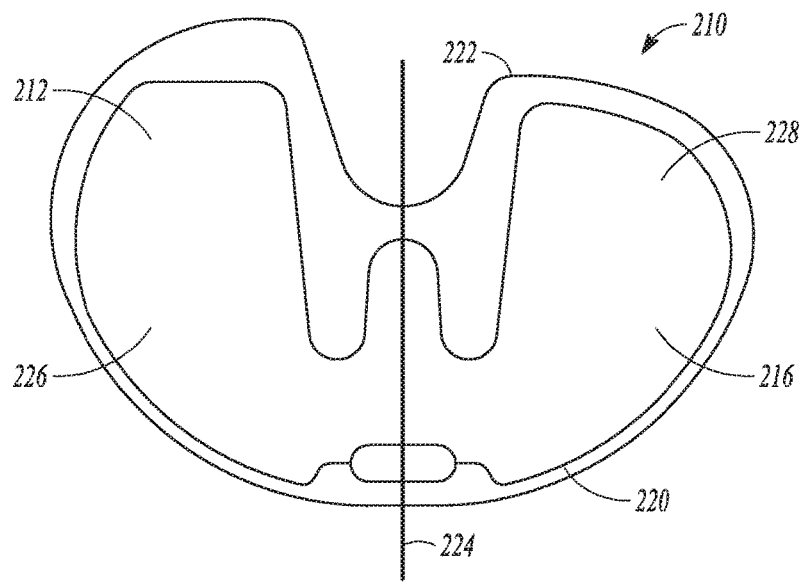
FIG. 3A is a plan view of a proximal side of a tibial implant for a left knee according to an example of the present application.
Figure 3B:
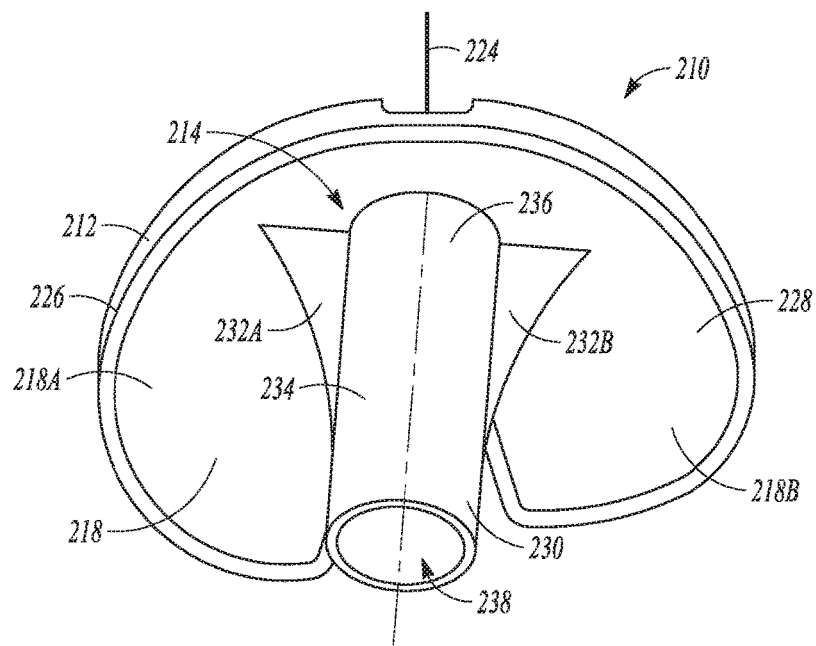
FIG. 3B is a perspective view of a distal portion of the tibial implant of FIG. 3A illustrating a fixation member canted relative to a distal surface of a baseplate according to an example of the present application.

FIGS. 3A and 3B show an example tibial implant 210 configured for a left knee (note difference from the configuration of FIG. 2 which is configured for the right knee). According to further examples the example of FIGS. 3A and 3B can be mirrored for use with the right knee. The tibial implant 210 includes a baseplate 212 and a fixation member 214 (FIG. 3B). The baseplate 212 includes a proximal surface 216 (FIG. 3A), a distal surface 218 (FIG. 3B), an anterior edge 220, a posterior edge 222, an anteroposterior axis 224, a lateral portion 226, and a medial portion 228. The fixation member 214 shown in FIG. 3B comprises a keel 230 and fins 232A and 232B. The keel 230 includes a medial portion 234, a lateral portion 236, and a receptacle 238.

In the example provided, the baseplate 212 and fixation member 214 are coupled together. As shown in FIG. 3A, the baseplate 212 can be configured at the proximal surface 216 to receive a tibial bearing component, for example. The distal surface 218 is disposed on an opposing side of the baseplate 212 from the proximal surface 216 and can be configured to interface with a resected proximal surface of a tibia. The distal surface 218 can include a medial portion 218A (corresponding to that of the medial portion 226) and a lateral portion 218B (corresponding to that of the lateral portion 228). Both the proximal surface 216 and the distal surface 218 extend from the anterior edge 220 to the posterior edge 222 of the baseplate 212.

As shown in FIG. 3A the anteroposterior axis 224 can divide the baseplate 212 into the medial portion 226 and the lateral portion 228. Thus, the medial portion 226 and the lateral portion 228 can be oriented relative to the anteroposterior axis 218. Although shown with an asymmetrically shaped medial portion 226 relative to the lateral portion 228, in some examples the medial portion 226 and the lateral portion 228 can be substantially symmetric relative to one another.

As shown in the example of FIG. 3B, the fixation member 214 can be coupled to and can extend both distally and medially from the distal surface 218 such that the fixation member 214 is oriented at an acute angle θ (FIG. 4) relative to the distal surface 218A of the medial portion 226 when viewed in the frontal or coronal plane. Put another way with reference to FIG. 2 for terminology and points of reference, the fixation member 214 can be provided with an angle (β>90° in reference to the tibial anatomical axis 122) to compensate for the varus orientation of the baseplate 212 on the resected proximal end surface 132 of the tibia 18. Thus, the fixation member 214 can configured to substantially align with a central axis (indicated by tibial anatomical axis 122 of FIG. 2) of the tibial diaphysis when the fixation member 214 is coupled to the distal surface 218 of the baseplate 212. This orientation of the fixation member reduces the risk that the fixation member 214 will perforate the lateral metaphysis or lateral diaphysis when the tibial component 210 is seated down into a position on top of the resected proximal end surface 132 of the tibia 18.

As shown in the example of FIG. 3B, the fixation member 214 is configured as a keel 230, however in other examples the fixation member 214 can comprise some other type of projection (e.g., a stem, a peg, or the like) that is configured for insertion into the metaphysis or diaphysis of the tibia. According to the example of FIG. 3B, the keel 230 can have fins 232A and 232B extending to the medial portion 226 and lateral portion 228, respectively. Additionally, the keel 230 can have the medial portion 234 be differently configured than the lateral portion 236. For example, the lateral portion 236 can have a greater surface area than the medial portion 234 as shown in the illustrated example of FIG. 3B due to the angling of the fixation member 214 relative to the distal surface 318 of the baseplate 212. Such angling can provide the lateral portion 236 with a greater distal extent than a distal extent of the medial portion 234.

As shown in FIG. 3B, the keel 230 can form the receptacle 238 which extends through a substantial portion of the keel 230. The receptacle 238 can receive a stem such as a stem 240 of FIGS. 4 and 5, for example. Further disclosure of various examples of keels with stems including coupling mechanisms between these two components and/or the baseplate are provided in U.S. Patent Application Publication 2013/0024001, entitled "ASYMMETRIC TIBIAL COMPONENTS FOR A KNEE PROSTHESIS", filed Jan. 23, 2013 and by U.S. Pat. No. 7,691,150, entitled "MODULAR PLATE AND KEEL PROVISONALS", filed Dec. 14, 2006, the entire disclosures of both of which are incorporated herein by reference.

Figure 4:
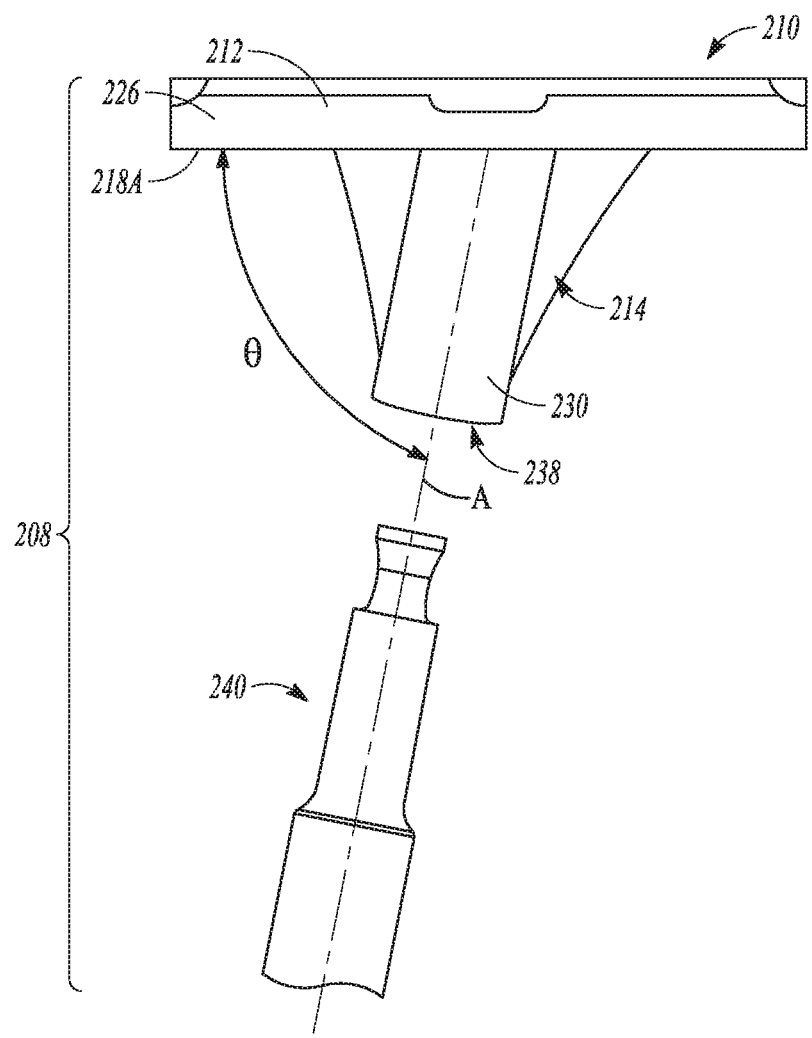
FIG. 4 is a view of an assembly in a coronal plane including the tibial implant of FIGS. 3A and 3B and a stem according to an example of the present application.

FIG. 4 shows an assembly 208 of the tibial implant 210 from FIGS. 2A and 2B with the stem 240 that can be configured to be received in the receptacle 238. Thus, the stem 240 is configured to be insertable into the keel 230 to couple together the stem 240 and the keel 230. One or both of the keel 230 and the stem 240 are configured to be removably attached to the baseplate 212. In the example of FIG. 4, the keel 230 has a female mating option (receptacle 238) where the stem 240 can be selected as a male counterpart. However, other configurations will be discussed subsequently. Thus, the keel 230 can be configured to couple to the baseplate 212 at the acute angle θ and coupling of the stem 240 with the keel 230 orients the stem 240 at substantially a same acute angle relative to the distal surface 218A of the medial portion 226 as the acute angle θ of the keel 230. In FIG. 4, the fixation member 214 includes a symmetric feature (e.g. the receptacle 238 and the stem 240) each having an axis of symmetry A. The acute angle θ can extend between the axis of symmetry A and the distal surface 218A of the medial portion 226.

Furthermore, FIGS. 3A to 4 illustrate an example where the keel 230 can be integrally formed with the baseplate 212 such that the two components comprise a single component. However, in other examples the keel 230 can be affixed by other mechanisms (weld, thread, interference fit, or the like) some of which allow the keel to be removable from the baseplate.

Figure 5:
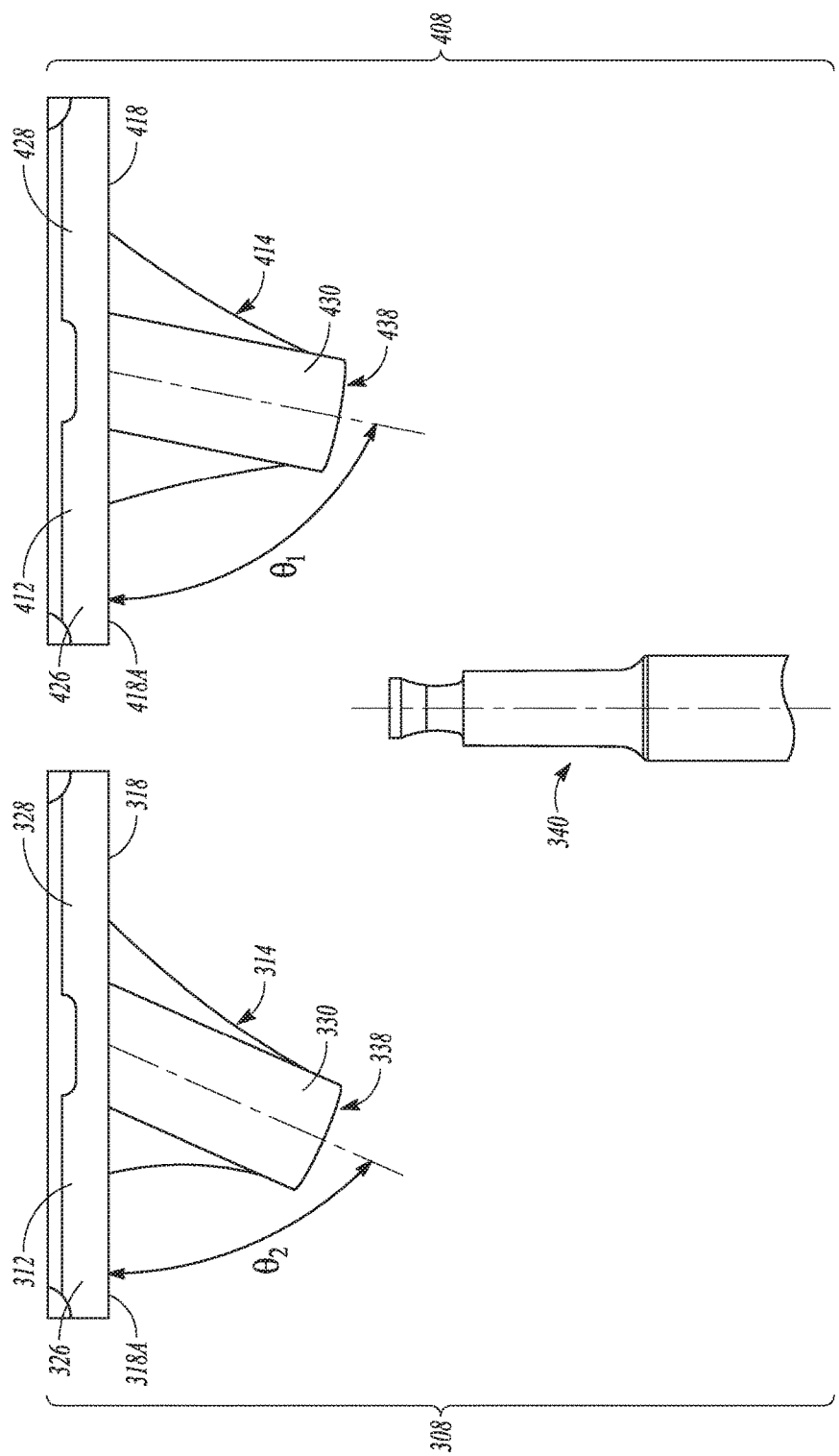
FIG. 5 is a view of two assemblies including tibial implants and other components according to an example of the present application.

FIG. 5 shows components that can comprise assemblies 308 and 408. In particular, when assembled together the components can comprise a tibial implant similar to those previously shown and discussed herein. As shown in the example of FIG. 5, the assemblies 308, 408 can include at least one baseplate (e.g., baseplate 312 and baseplate 412). As with prior discussed embodiments, each baseplate 312, 412 can have a medial portion 326, 426 and a lateral portion 328, 428. Furthermore, each of the medial portion 326, 426 and the lateral portion 328, 428 can have a distal surface 318, 418 configured to interface with a resected proximal surface of a tibia.

The assemblies 308, 408 also can include at least one of a plurality of fixation members 314, 414. Each of the plurality of fixation members 314, 414 can be configured to attach to and extend both distally and medially from the distal surface 318, 418 such that each fixation member 314, 414 of the plurality of fixation members 314, 414 is oriented at an acute angle $\theta_1$, $\theta_2$ relative to the distal surface 318A, 418A of the medial portion 326, 426 when viewed in the frontal or coronal plane. Each of the plurality of fixation members 314, 414 can be configured to differ from others of the plurality of fixation members 314, 414 such that the acute angle $\theta_2$, $\theta_1$ formed by each of the plurality of fixation members 314, 414 when coupled to the baseplate 312, 412 would differ in degree.

More particular, a keel 330, 430 can be coupled to and extend both distally and medially relative to the distal surface 318, 412 such that the keel 330, 430 creates the acute angle $\theta_1$, $\theta_2$ between the keel 330, 430 and the distal surface 318A, 418A of the medial portion 326, 426 when viewed in the frontal or coronal plane. A stem 340 can be configured to couple with one or both of the keel 330, 430 and the baseplate 312, 412 and can be configured to removably insert within a receptacle 338, 438 of the keel 330, 430.

It should be noted that although illustrated as assemblies 308, 408 that include almost entirely separate components, in some examples a component such as one or more of the baseplates 312, 412, keels 330, 430, and/or stem 340 can be configured to universally couple with others of the components. For example, in FIG. 5 the plurality of fixation members 314, 414 can comprise a plurality of keels 330, 430 (each keel 330, 430 can have a different configuration) and a single stem 340. The single stem 340 can have only a single configuration and can be configured to universally couple with any of the plurality of keels 330, 430. As shown in FIG. 5, the keels 330, 430 can comprise one of a plurality of keels (e.g., 330, 430, and so on) each keel 330, 430 can be configured to form a different acute angle (e.g., $\theta_1$, $\theta_2$, and so on) when coupled to the baseplate 312, 412. Although a plurality of baseplates 312, 412 are shown in FIG. 5, in some examples a single baseplate can be utilized with the assemblies and can be configured to couple to any of the plurality of keels (e.g., 330, 430).

Figure 6:
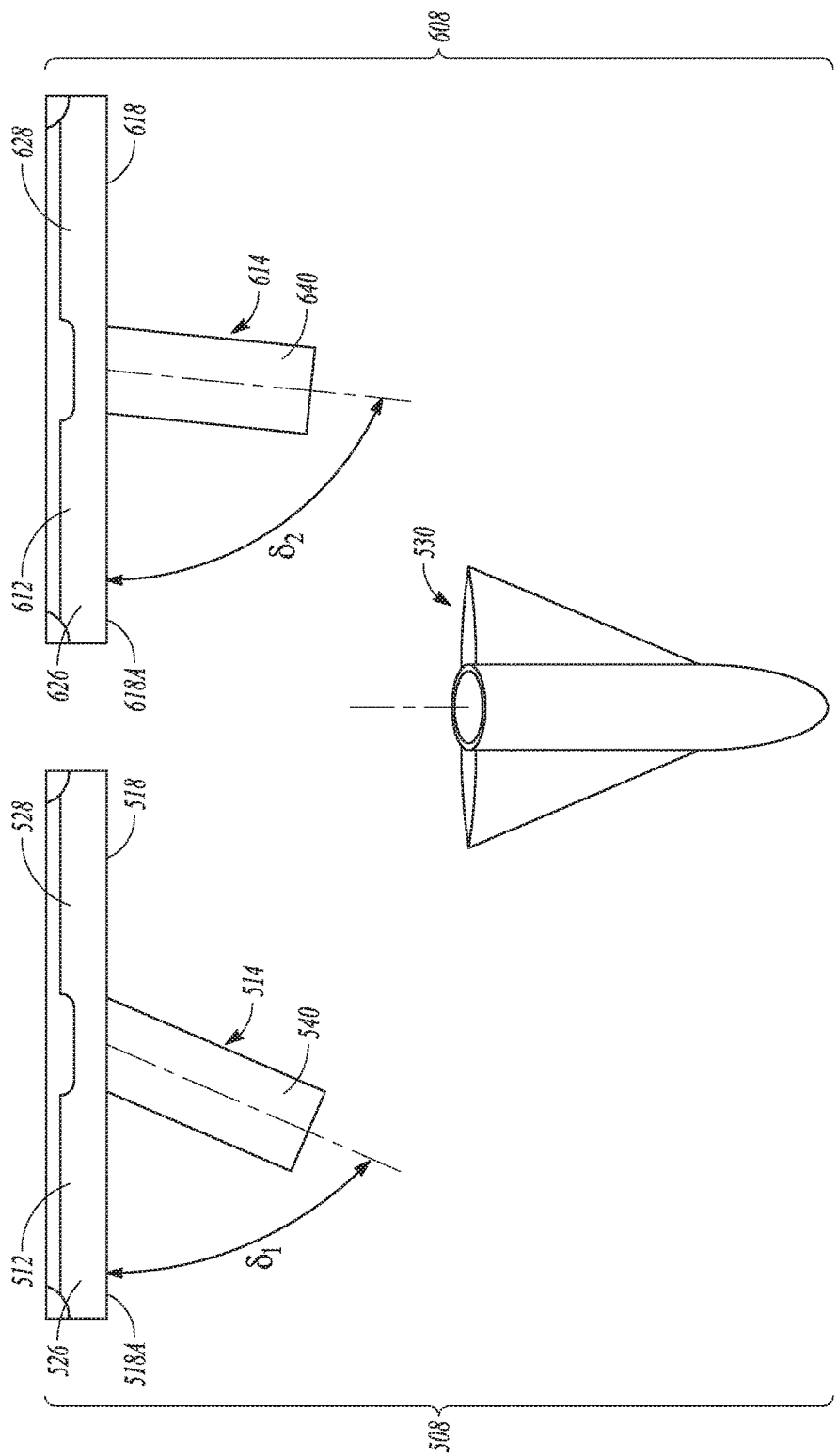
FIG. 6 is a view of two assemblies including tibial implants and other components according to another example of the present application.

FIG. 6 shows assemblies 508, 608 according to further examples. According to the examples of FIG. 6, the assemblies 508, 608 can include at least one baseplate (e.g., baseplate 512 and baseplate 612). As with prior discussed embodiments, each baseplate 512, 612 can have a medial portion 526, 626 and a lateral portion 528, 628 oriented relative to an anteroposterior axis (not shown). Furthermore, each baseplate 512, 612 can have a distal surface 518, 618 configured to interface with a resected proximal end surface 132 (FIG. 2) of a tibia.

The assemblies 508, 608 also can include at least one of a plurality of fixation members 514, 614. Each of the plurality of fixation members 514, 614 can be configured to attach to and extend both distally and medially from the distal surface 518, 618 such that each fixation member 514, 614 of the plurality of fixation members 514, 614 is oriented at an acute angle $\delta_1$, $\delta_2$ relative to the distal surface 518A, 618A of the medial portion 526, 626 when viewed in the frontal or coronal plane. Each of the plurality of fixation members 514, 614 can be configured to differ from others of the plurality of fixation members 514, 614 such that the acute angle $\delta_1$, $\delta_2$ formed by each of the plurality of fixation members 514, 614 when mounted to the baseplate 512, 612 would differ in degree. The examples of FIG. 6 utilize a plurality of stems 540, 640 and a single keel 530. Each stem 540, 640 can be configured to couple to the baseplate 512 and/or 612 at the acute angle $\delta_1$, $\delta_2$. Coupling of the keel 530 with the stem 540 can orient the keel 530 at substantially a same acute angle relative to the distal surface 518A, 618A of the medial portion 526, 626 as the acute angle $\delta_1$, $\delta_2$.

It should be noted similar to assemblies 308, 408 the assemblies 508, 608 can be have one or more components configured to universally couple with others of the components of the assemblies 508, 608. For example, in FIG. 6 the plurality of fixation members 514, 614 can comprise the plurality of stems 540, 640 (each keel 330, 430 can have a different configuration) and a single keel 530. Thus, according to some examples the keel 530 can have only a single configuration and can be configured to universally couple with any of the plurality of stems 540, 640. As shown in FIG. 6, the stems 540, 640 can comprise one of a plurality of stems (e.g., 540, 640, and so on) each keel 540, 640 can be configured to form a different acute angle (e.g., $\delta_1$, $\delta_2$, and so on) when coupled to the baseplate 512, 612.

An example method of performing a knee arthroplasty using a tibial implant such as those discussed herein can include resecting a proximal surface of a tibia to expose a tibial metaphysis, and attaching a tibial implant to the resected surface at a distal surface of a baseplate of the tibial implant. The tibial implant can have a fixation member which is configured to generally align with a central axis of the tibial diaphysis (e.g., indicated by tibial anatomical axis 122 of FIG. 2) when coupled to the distal surface of the baseplate. According to further examples the method can include determining a desired angle based on degree of varus between the distal surface of the baseplate and the central axis of the tibial diaphysis, selecting from a plurality of fixation members that are configured to achieve the desired angle when coupled to the baseplate, and coupling the selected fixation member to the tibial baseplate.

Figure 7A:
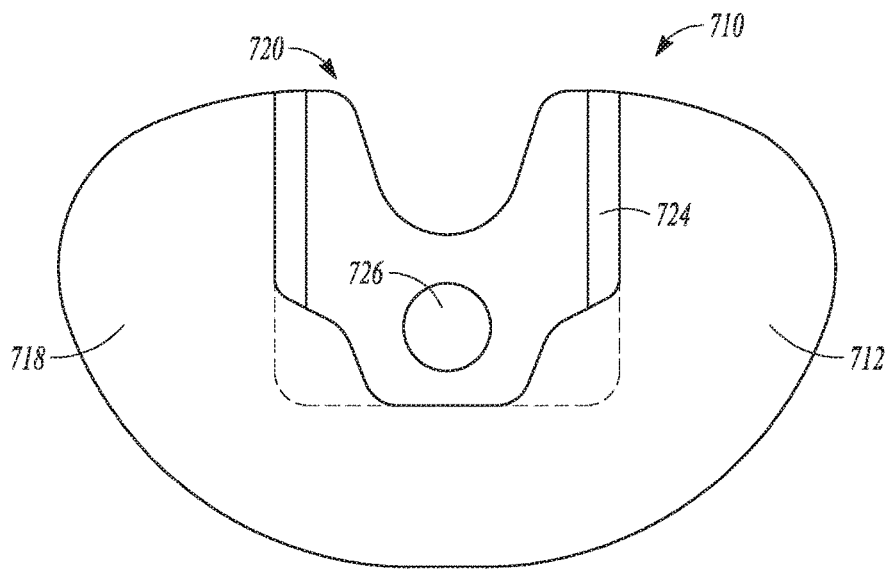
FIG. 7A is a plan view of a distal side of a tibial implant according to yet another example of the present application.
Figure 7B:
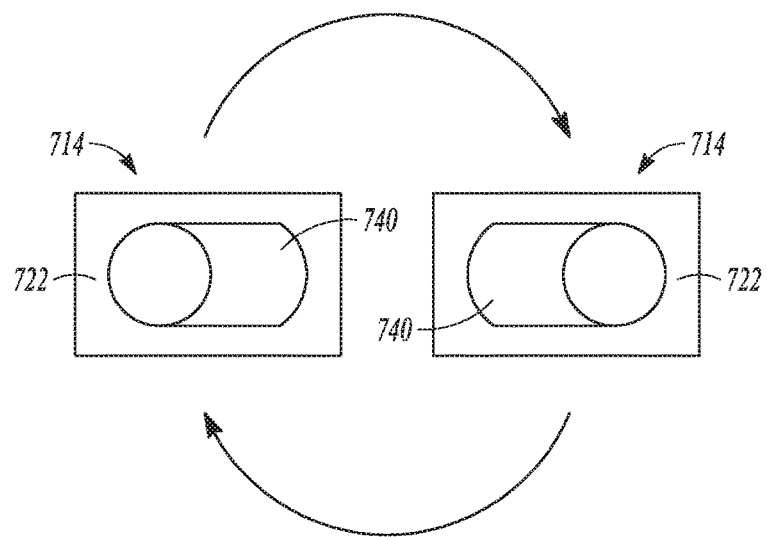
FIG. 7B is a plan view of a fixation member in two orientations according to example of the present application.
Figure 7C:
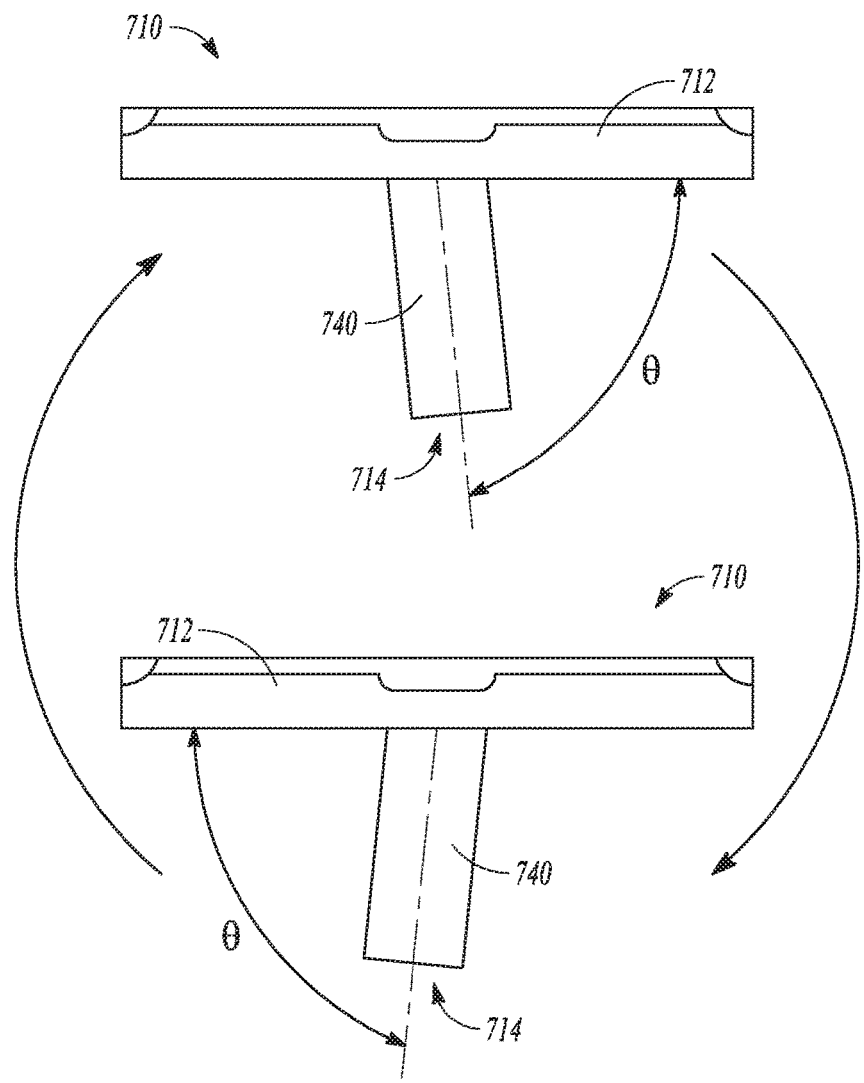
FIG. 7C is a coronal plan view of the tibial implant of FIG. 7A coupled to the fixation member of FIG. 7B with the fixation member in a first orientation such as is shown in FIG. 7B and with the fixation member in a second orientation such as is shown in FIG. 7B according to an example of the present application.

FIGS. 7A to 7C show another example of a tibial implant 710 where a baseplate 712 and fixation member 714 are configured such that the fixation member 714 is adjustable relative to the baseplate 712. The tibial implant 710 can include the baseplate 712 and the fixation member 714 similar to those previously described. Thus, the baseplate 712 can include a distal surface 718 and the fixation member 714 can comprise a stem 740 (FIGS. 7B and 7C) configured to mate with one or more keels (not shown). However, the baseplate 712 can also include a coupling feature 720 (FIG. 7A) disposed at the distal surface 718.

The coupling feature 720 can be configured to couple with a base 722 (FIG. 7B) of the stem 740 with the base 722 and the stem 740 assembly in multiple orientations. As illustrated and described according to the example of FIGS. 7A to 7C, the stem 740 can be configured to be adjustable 180° relative to the baseplate 712 by simply reversing the orientation of the base 722 (shown in FIG. 7B) and then recoupling the base 722 and the stem 740 to the baseplate 712. Therefore, FIGS. 7A to 7C show an example where the baseplate 712 and fixation member 714 that are configured such that the fixation member 714 can be coupled to the baseplate 712 in at least two orientations including to create a first configuration for a right knee and a second configuration for a left knee. According to other examples, rather than being configured to be adjustable 180° relative to the baseplate, the fixation member can be clocked to be incrementally adjustable both in the medial-lateral direction but also in the anterior-posterior direction. Thus, in some examples the fixation member can be re-orientable relative to the baseplate to form a plurality of different configurations.

More particularly, the coupling feature 720 can comprise fixation mechanisms known in the art such as those that use a slot, groove, flange, male/female connection, interference, tab, fastener, pin, or other mechanisms to couple the base 722 to the baseplate 712. According to the example of FIG. 7A, the coupling feature 720 comprises grooves 724 adapted to receive corresponding features of the base 722 which is inserted from a posterior toward an anterior of the baseplate 712. A fastener (not shown) can be received in hole 726 in the baseplate 712 and can insert into or abut the base 722 once the base 722 is moved into the desired position. This can further lock the base 722 relative to the baseplate 712. FIG. 7A provides only one example of a coupling feature others including those that utilize a different insertion direction and/or coupling mechanism(s) are contemplated.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for forming a tibial implant configured for attachment to a tibia in a knee arthroplasty, the system comprising:
   one or more baseplates having a lateral portion and a medial portion oriented relative to an anteroposterior axis, each of the lateral portion and the medial portion having a distal surface configured to interface with a resected proximal surface of a tibia;
   a plurality of fixation members each of the plurality of fixation members being configured to couple to the baseplate and extend both distally and medially from the baseplate such that each fixation member of the plurality of fixation members is oriented at an acute angle relative to the distal surface of the medial portion, and wherein each of the plurality of fixation members is configured to differ from others of the plurality of fixation members such that the acute angle formed by each of the plurality of fixation members, when mounted to the baseplate, differs in degree.

2. The system of claim 1, wherein the plurality of fixation members comprises a plurality of keels each having a different configuration and a single stem having a single configuration, wherein the single stem is configured to universally couple with any of the plurality of keels.

3. The system of claim 1, wherein the plurality of fixation members comprises a plurality of stems each having a different configuration and a single keel having a single shape, wherein the single keel is configured to universally couple with any of the plurality of stems.

4. The system of claim 1, wherein the one or more baseplates and the plurality of fixation members are configured such that one of the plurality of fixation members is couplable with one of the one or more baseplates in at least two orientations including to create a first configuration for a right knee and a second configuration for a left knee.

5. A system for forming a tibial implant configured for attachment to a tibia in a knee arthroplasty, the system comprising:
   one or more baseplates having a lateral portion and a medial portion oriented relative to an anteroposterior axis, each of the lateral portion and the medial portion having a distal surface configured to interface with a resected proximal surface of a tibia;
   a plurality of fixation members each of the plurality of fixation members being configured to couple to the baseplate and extend both distally and medially from the baseplate such that each fixation member of the plurality of fixation members is oriented at an acute angle relative to the distal surface of the medial portion, and wherein each of the plurality of fixation members is configured to differ from others of the plurality of fixation members such that the acute angle formed by each of the plurality of fixation members, when mounted to the baseplate, differs in degree, wherein each of the plurality of fixation members comprise a combination of a keel and a stem that are configured for insertion into a metaphysis and/or diaphysis of the tibia.

6. The system of claim 5, wherein at least one of the keel and stem are configured to be removably attached to the baseplate.

7. The system of claim 6, wherein at least one of the keel and stem are configured to be adjustable 180° relative to at least one of the one or more the baseplates such that the tibial implant is configured for use with both a left tibia and a right tibia.

8. The system of claim 5, wherein the stem and keel are configured to couple together, and wherein the stem is configured to couple to the baseplate at the acute angle and coupling of the keel with the stem orients the keel at substantially a same acute angle relative to the distal surface of the medial portion as the acute angle.

9. The system of claim 5, wherein the stem and keel are configured to couple together, and wherein the keel is configured to couple to at least one of the one or more the baseplates at the acute angle and coupling of the stem with the keel orients the stem at substantially a same acute angle relative to the distal surface of the medial portion as the acute angle.

10. A system for forming a tibial implant configured for attachment to a tibia in a knee arthroplasty, the system comprising:
    one or more baseplates having a lateral portion and a medial portion oriented relative to an anteroposterior axis, each of the lateral portion and the medial portion having a distal surface configured to interface with a resected proximal surface of a tibia;

a plurality of fixation members each of the plurality of fixation members being configured to couple to the baseplate and extend both distally and medially from the baseplate such that each fixation member of the plurality of fixation members is oriented at an acute angle relative to the distal surface of the medial portion, and wherein each of the plurality of fixation members is configured to differ from others of the plurality of fixation members such that the acute angle formed by each of the plurality of fixation members, when mounted to the baseplate, differs in degree, wherein the one or more baseplates and the plurality of fixation members are configured such that one of the plurality of fixation members is adjustable 180° relative to one of the one or more baseplates such that the tibial implant is configured for use with both a left tibia and a right tibia.

11. The system of claim 10, wherein each of the plurality of fixation members comprise a combination of a keel and a stem that are configured for insertion into a metaphysis and/or diaphysis of the tibia.

12. The system of claim 11, wherein at least one of the keel and stem are configured to be removably attached to the baseplate.

13. The system of claim 12, wherein at least one of the keel and stem are configured to be adjustable 180° relative to at least one of the one or more the baseplates such that the tibial implant is configured for use with both a left tibia and a right tibia.

14. The system of claim 10, wherein the stem and keel are configured to couple together, and wherein the stem is configured to couple to the baseplate at the acute angle and coupling of the keel with the stem orients the keel at substantially a same acute angle relative to the distal surface of the medial portion as the acute angle.

15. The system of claim 10, wherein the stem and keel are configured to couple together, and wherein the keel is configured to couple to at least one of the one or more the baseplates at the acute angle and coupling of the stem with the keel orients the stem at substantially a same acute angle relative to the distal surface of the medial portion as the acute angle.

16. The system of claim 10, wherein at least one of the plurality of fixation members includes a symmetric feature having an axis of symmetry, and wherein the acute angle is measured between the axis of symmetry and the distal surface of the medial portion.

17. The system of claim 10, wherein at least one of the plurality of includes a lateral portion and a medial portion, and wherein the medial portion has a greater surface area than the lateral portion.

* * * * *

UNITED STATES PATENT AND TRADEMARK OFFICE
CERTIFICATE OF CORRECTION

PATENT NO. : 10,136,997 B2  
APPLICATION NO. : 15/267826  
DATED : November 27, 2018  
INVENTOR(S) : Edward R. Yager Page 1 of 1

It is certified that error appears in the above-identified patent and that said Letters Patent is hereby corrected as shown below:

On the Title Page

On page 4, in Column 1, under "Other Publications", Line 30, delete "Sep. 26, 2017"," and insert --Jun. 26, 2017",-- therefor On page 4, in Column 2, under "Other Publications", Line 22, delete "Offce" and insert --Office-- therefor On page 4, in Column 2, under "Other Publications", Line 32, delete "Aug. 17, 2015"," and insert --Jun. 17, 2015",-- therefor In the Claims In Column 14, Line 25, in Claim 17, after "of", insert --fixation members--

Signed and Sealed this  
Twenty-eighth Day of April, 2020

Andrei Iancu  
*Director of the United States Patent and Trademark Office*